(12) United States Patent
Saar et al.

(10) Patent No.: US 8,983,594 B2
(45) Date of Patent: Mar. 17, 2015

(54) ELECTRONIC CONTROL OF DRUG DELIVERY SYSTEM

(75) Inventors: David Saar, Titusville, NJ (US); Bogdan Mariusz Baudis, Stoneham, MA (US); Rainuka Gupta, Cambridge, MA (US); Vaishali Vilas Kamat, Arlington, MA (US); Matthew Kent Reich, Medford, MA (US); Rajagopalan Srinivasan, Cambridge, MA (US)

(73) Assignee: NuPathe, Inc., Malvern, PA (US)

( * ) Notice: Subject to any disclaimer, the term of this patent is extended or adjusted under 35 U.S.C. 154(b) by 325 days.

(21) Appl. No.: 12/648,726

(22) Filed: Dec. 29, 2009

(65) Prior Publication Data

US 2010/0262066 A1 Oct. 14, 2010

Related U.S. Application Data

(60) Provisional application No. 61/141,377, filed on Dec. 30, 2008.

(51) Int. Cl.
*A61N 1/30* (2006.01)
*A61N 1/04* (2006.01)
*A61N 1/32* (2006.01)

(52) U.S. Cl.
CPC .............. *A61N 1/303* (2013.01); *A61N 1/0436* (2013.01); *A61N 1/325* (2013.01); *A61N 1/0448* (2013.01)
USPC .......................................................... 604/20

(58) Field of Classification Search
USPC .................. 604/19, 20, 21, 500, 501
See application file for complete search history.

(56) References Cited

U.S. PATENT DOCUMENTS

| | | | |
|---|---|---|---|
| 4,141,359 A | | 2/1979 | Jacobsen et al. |
| 5,042,975 A | * | 8/1991 | Chien et al. ..................... 604/20 |
| 5,047,007 A | | 9/1991 | McNichols et al. |
| 5,246,418 A | | 9/1993 | Haynes et al. |
| 5,254,007 A | | 10/1993 | Eagan |
| 5,426,387 A | | 6/1995 | Teillaud et al. |

(Continued)

FOREIGN PATENT DOCUMENTS

| | | |
|---|---|---|
| EP | 0558409 A1 | 9/1993 |
| EP | 0847775 A1 | 6/1998 |

(Continued)

OTHER PUBLICATIONS

International Search Report and Written Opinion for Application No. PCT/US09/069673, mailed on Apr. 22, 2010.

(Continued)

*Primary Examiner* — Kami A Bosworth
(74) *Attorney, Agent, or Firm* — McCarter & English, LLP; Danielle L. Herritt; Kia L. Freeman

(57) ABSTRACT

In an exemplary embodiment, a drug delivery device for driving an electrotransport current through a body surface of a user is provided. The device includes a patch with two electrodes and one or more reservoirs storing a therapeutic agent. The one or more reservoirs release the therapeutic agent into the body surface of the user when the reservoirs are positioned over the electrodes to form an electrical path for the electrotransport current. The device includes a controller which controls a controllable power supply to drive the electrotransport current through the body surface of the user in a predetermined profile.

27 Claims, 13 Drawing Sheets

(56) References Cited

U.S. PATENT DOCUMENTS

| | | | |
|---|---|---|---|
| 5,499,967 A | 3/1996 | Teillaud et al. | |
| 5,983,130 A * | 11/1999 | Phipps et al. | 604/20 |
| 6,035,234 A | 3/2000 | Riddle et al. | |
| 6,167,301 A | 12/2000 | Flower et al. | |
| 6,377,848 B1 | 4/2002 | Garde et al. | |
| 6,385,488 B1 | 5/2002 | Flower et al. | |
| 6,402,732 B1 | 6/2002 | Flower et al. | |
| 6,522,919 B1 | 2/2003 | Flower et al. | |
| 6,678,555 B2 | 1/2004 | Flower et al. | |
| 6,842,640 B2 | 1/2005 | Riddle et al. | |
| 7,708,731 B2 | 5/2010 | Riddle et al. | |
| 7,937,141 B1 | 5/2011 | Inoue et al. | |
| 2003/0013753 A1 * | 1/2003 | Aung-Din | 514/419 |

FOREIGN PATENT DOCUMENTS

| | | |
|---|---|---|
| WO | 91/16943 A1 | 11/1991 |
| WO | 95/06497 A1 | 3/1995 |
| WO | 96/17651 A1 | 6/1996 |
| WO | 96/30077 A1 | 10/1996 |
| WO | 96/39223 A1 | 12/1996 |
| WO | 96/39224 A1 | 12/1996 |
| WO | 97/11743 A1 | 4/1997 |
| WO | WO 97/11743 A1 | 4/1997 |
| WO | 99/30773 A1 | 6/1999 |
| WO | WO 99/30775 A1 | 6/1999 |

OTHER PUBLICATIONS

International Preliminary Report on Patentability issued in International Application No. PCT/US09/069673, issued Jul. 5, 2011 (10 pages).

Examination Report issued in New Zealand Patent Application No. 593928, dated Sep. 19, 2012.

Official Notification issued in Israeli Patent Application No. 593928, dated Jan. 15, 2013.

Office Action issued in Eurasian Patent Application No. 201100891, dated Jan. 16, 2013.

Notification of First Office Action by the Chinese State Intellectual Property Office for Application No. 200980157664.6, dated Jul. 4, 2013 (6 pages) with English translation (8 pages).

Patent Examination Report No. 1 issued by the Australian Patent Office for Patent Application No. 2009335085 on Jan. 17, 2014 (3 pages).

First Examination Report from the New Zealand Intellectual Property Office for Patent Application No. 622157 dated Mar. 21, 2014 (2 pages).

Notice of Reasons for Rejection issued by the Japan Patent Office for Patent Application No. 2011-544581 on Jan. 7, 2014 (4 pages) with English translation (5 pages).

* cited by examiner

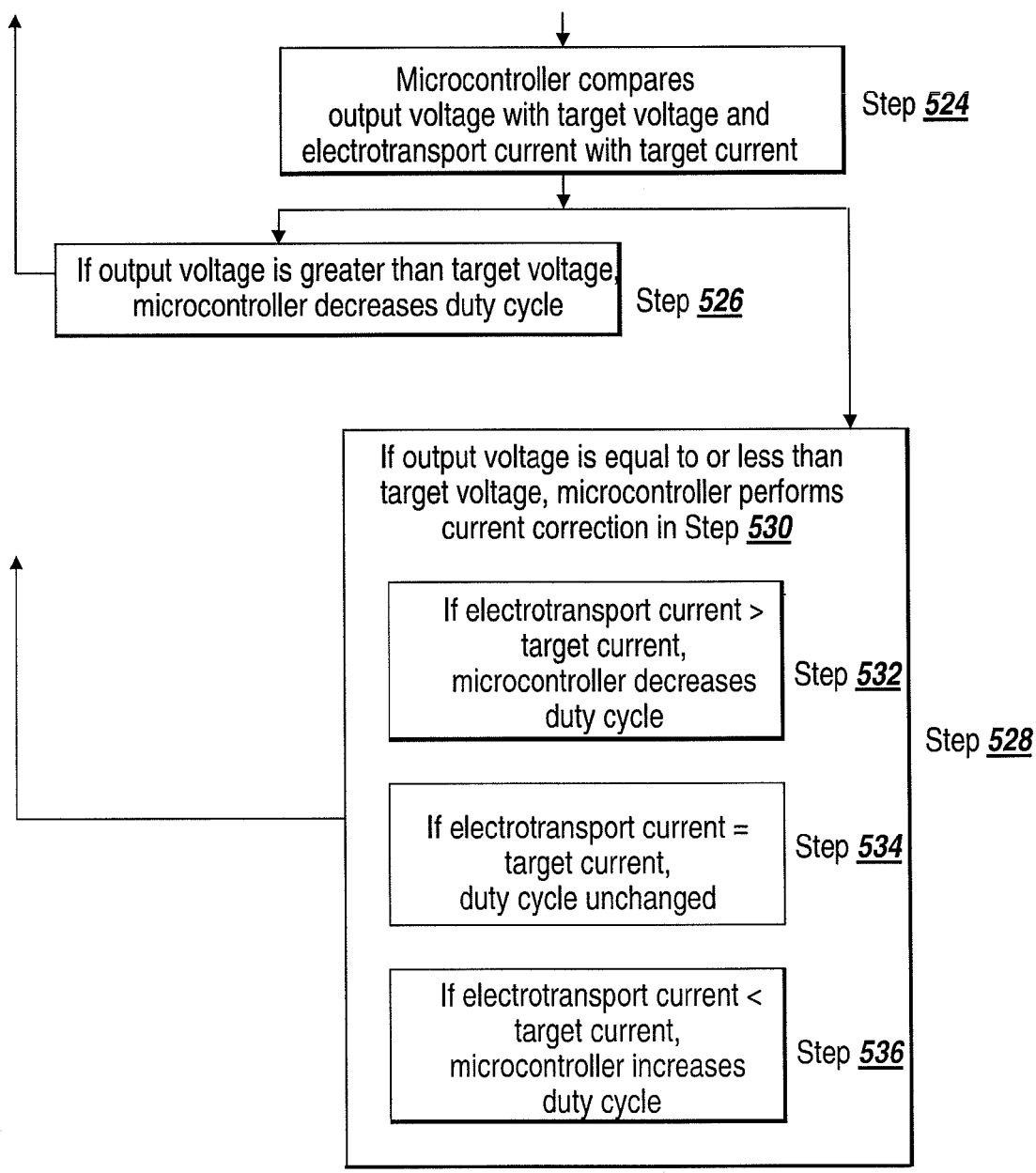
*Fig. 11 contd.*

ELECTRONIC CONTROL OF DRUG DELIVERY SYSTEM

RELATED APPLICATIONS

This application claims priority to U.S. Provisional Application Ser. No. 61/141,377, filed on Dec. 30, 2008, and titled "Electronic Control Of Drug Delivery System", which is incorporated herein by reference in its entirety.

BACKGROUND

Drug delivery is the method or process of delivering a pharmaceutical drug or agent to achieve a therapeutic effect in a user (defined as humans or animals). Drug delivery technologies are intended to control or modify drug release profiles for the benefit of improving product efficacy and patient convenience and compliance. Common methods of parenteral delivery include the following routes: intravenous, intramuscular, subcutaneous, intradermal, transdermal, inhalational, etc.

Drug delivery technologies may include the use of electronic circuits to control the duration of administration or the dose (amount) of a pharmaceutical drug or agent. Iontophoresis is an example of a drug delivery technology that implements electronic control over the administration of a drug. Iontophoresis utilizes an electrical current to transport a drug or agent transdermally, i.e. through the user's skin, in a safe and effective manner.

SUMMARY

Exemplary embodiments may provide methods, systems and apparatuses for a drug delivery system or device which implements electronic control over the release of a pharmaceutical drug or agent. The terms "drug delivery system" and "device" can be used interchangeably in the context of the present invention. In exemplary embodiments, the electronic control may control an electrotransport current which transdermally delivers an agent to a user. Exemplary embodiments may achieve a desired profile in time of the agent in the user's body by controlling a profile in time of the electrotransport current.

Exemplary embodiments may control the electrotransport current using a linear regulator or any type of a switching regulator.

In an exemplary embodiment, the electrotransport current may be controlled using pulse width modulation (PWM), e.g. by adjusting the duty cycle of a PWM power supply. Exemplary embodiments may generate interrupts at regular intervals, and perform current correction upon the generation of each interrupt. Exemplary embodiments may detect the electrotransport current flowing through the user's skin, and compare it to a dynamic current value representative of the target current. The target current may be based on the desired current profile. Based on a comparison of the electrotransport current and the dynamic value representative of the target current, exemplary embodiments may increase, decrease or retain the current duty cycle of the PWM power supply.

Exemplary embodiments may also include methods and apparatuses used for the testing of the electronic connection of drug delivery devices (i.e., iontophoretic drug delivery systems as taught herein). Such exemplary apparatuses may include an electrode patch continuity tester that is adapted for use in the testing and verification of the connections of the iontophoretic drug delivery system.

Exemplary methods may also include methods for the testing and verification of the electronic connections of the iontophoretic drug delivery system.

Exemplary methods may also include methods for testing, measuring or otherwise quantifying the capacity of the electrode of an iontophoretic drug delivery system, as described herein, to deliver a drug.

In one exemplary embodiment, a method of driving an electrotransport current through an animal body surface using a pulse width modulation (PWM) controller is provided. The method includes driving the electrotransport current through the animal body surface using a PWM power supply. The method also includes generating one or more interrupts at predetermined intervals using a timer, and turning off the PWM power supply using the PWM controller when the one or more interrupts are generated. The method further includes controlling a duty cycle of the PWM power supply using the PWM controller at least based on a present value of the electrotransport current and a dynamic value representative of a target electrotransport current.

In a further exemplary embodiment, a drug delivery device for driving an electrotransport current through an animal body surface is provided. The device includes a first electrode, a second electrode, a controller (e.g. a programmable processor) configurable, programmable, or both to control an electrical current flowing between the first and second electrodes, a first conductive reservoir holding a first conductive medium and a therapeutic drug or agent to be positioned over the first electrode, a second conductive reservoir holding a second conductive medium and optionally an ion source to be positioned over the second electrode to form an electrical path for the electrical current. The device also includes a pulse width modulation (PWM) power supply for applying an output voltage across the animal body surface, and driving the electrotransport current through the animal body surface. The device further includes a controller to drive the electrotransport current through the animal body surface in a predetermined profile. The controller has a current monitor, a voltage monitor and a voltage regulator for performing an output voltage correction to adjust the electrotransport current.

BRIEF DESCRIPTION OF THE DRAWINGS

Exemplary embodiments will be described below relative to the following drawings in which like reference characters refer to the same parts throughout the different views.

DETAILED DESCRIPTION

Figure 1:
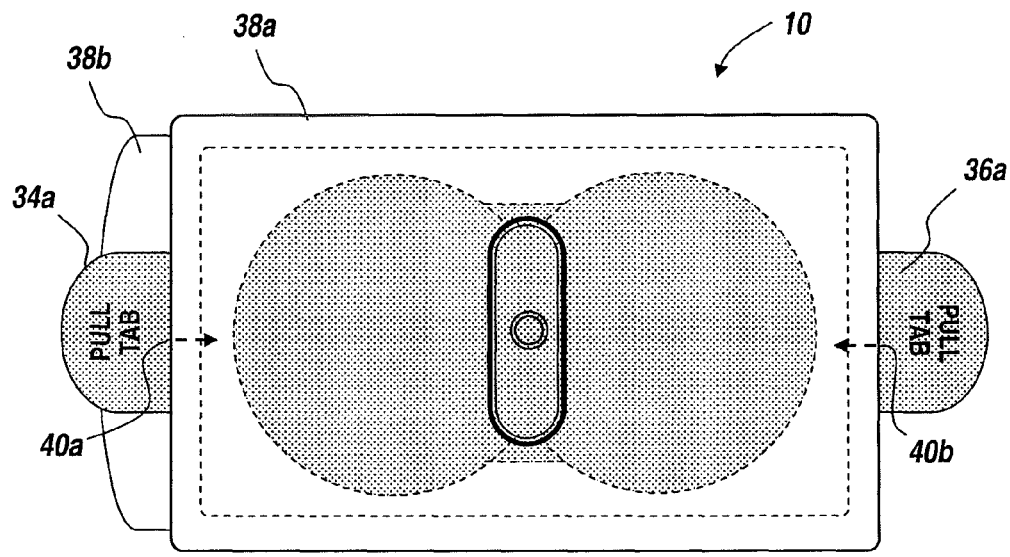
FIG. 1 depicts a top view of an exemplary self-contained pre-packaged iontophoretic drug delivery system.

Exemplary embodiments may provide methods, systems and apparatuses for a drug delivery system which implements electronic control over the release of a pharmaceutical drug or agent in a user. In exemplary embodiments, the electronic control may control an electrotransport current which transdermally delivers a drug to a user. Exemplary embodiments may achieve a desired profile in time and dosage of the drug in the user's body (e.g., a drug delivery profile and/or a plasma concentration profile) by controlling a profile in time of the electrotransport current.

Exemplary embodiments may control the electrotransport current by employing a power supply which is controllable using a linear regulator or any type of a switching regulator. In an exemplary embodiment, the power supply may be controllable by pulse width modulation (PWM). Such control of the drug delivery profile optimizes efficacy and safety of the drug, and allows automatic compliance of the drug regimen without the user having to monitor or alter the settings of the system during dosing.

Exemplary embodiments may regulate the electrotransport current by adjusting the duty cycle of the PWM power supply. Exemplary embodiments may generate interrupts at intervals, and perform current correction, if necessary, upon the generation of each interrupt. Exemplary embodiments may detect the electrotransport current flowing through the user's skin and compare it to a dynamic value representative of the target current. The target current may be based on the desired current profile. Based on a comparison of the electrotransport current and the dynamic value representative of the target current value, exemplary embodiments may increase, decrease or retain the current duty cycle of the PWM power supply.

Before continuing with the remainder of the description, it may be helpful to first define some terms as used through out the specification and claims.

The terms "user" and "subject" are used interchangeably herein, and include animals (e.g., mammals, e.g., cats, dogs, horses, pigs, cows, sheep, rodents, rabbits, squirrels, bears, and primates (e.g., chimpanzees, gorillas, and humans)) which may be treatable by the methods, systems and apparatuses of the present invention.

The term "drug" or "agent" includes any drug or agent which is capable of being administered in a therapeutically effective amount to a user employing the devices of the present invention. The present invention can be used to administer agents of different molecular sizes and charges. As used herein, a drug or agent may be a drug or other biologically active agent.

As used herein, the term "drug" and "therapeutic drug" are used interchangeably.

As used herein, the term "agent" and "therapeutic agent" are used interchangeably.

The term "drug delivery system" includes any system controlled by an electronic circuit to deliver a drug or an agent in a therapeutically effective manner. Examples of a drug delivery system include, but are not limited to, an iontophoretic system, an intravenous (IV) drip, an internal or external pump, an injected drug or agent, and an inhaled drug or agent. As used herein, the terms "system" and "device" are interchangeable.

As used herein, the term "computer readable media" refers to media that may store information or code, for example, magnetic discs, optical discs, and memory devices (e.g., flash memory devices, static RAM (SRAM) devices, dynamic RAM (DRAM) devices, or other memory devices).

Certain exemplary embodiments are described herein to provide an overall understanding of the principles of the structure, function, manufacture, and use of the methods, systems and apparatuses disclosed herein. One or more examples of these embodiments are illustrated in the accompanying drawings. The methods, systems and apparatuses specifically described herein and illustrated in the accompanying drawings are non-limiting exemplary embodiments, and the scope of the present invention is defined solely by the claims. The features illustrated or described in connection with one exemplary embodiment may be combined with the features of other embodiments. Such modifications and variations are intended to be included within the scope of the present invention.

Figure 2:
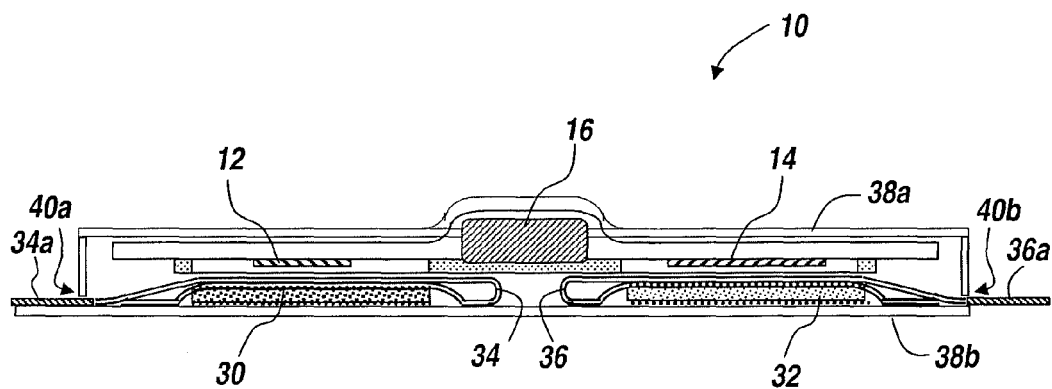
FIG. 2 depicts a side view of the exemplary iontophoretic drug delivery system depicted in FIG. 1.

FIGS. 1 and 2 depict an exemplary embodiment of a drug delivery system 10 which uses iontophoresis to transdermally deliver a drug to a user. Iontophoresis is a method of applying a current to a user's skin to administer an agent to the user's body through the skin of the user. The drug delivery system 10 of FIGS. 1 and 2 may be packaged as a patch which may be applied to the skin of the user and removed after the drug has been delivered. Some thicknesses in FIG. 2 are exaggerated for illustrative purposes.

As depicted by the cross-sectional side view of FIG. 2, the drug delivery system 10 may include a first electrode 12 and a second electrode 14. In an exemplary embodiment, the electrodes 12 and 14 may be round, circular, oval or any other geometrically suitable shape, or coated wires. In a further exemplary embodiment, the wires may be coated with zinc or silver and/or silver/silver chloride.

In an exemplary embodiment, the electrodes 12 and 14 may further comprise a polyester film. One suitable polyester film is a biaxially-oriented polyethylene terephthalate polyester film sold under the trademark MYLAR. MYLAR film is an advantageous material because of its thinness and flexibility. The polyester film of the electrodes 12 and 14 may be screen-printed or etched on such films with conductive ink including silver/silver chloride. The polyester film may further include a dielectric coating to provide electrical insulation. In an exemplary embodiment, the electrodes 12 and 14 may be affixed to the body of a user using fixing tape. In a further embodiment, components, like microprocessors and batteries, may be affixed directly onto the polyester film with glue, conductive glue, solder, or tabs. In another exemplary embodiment, the electrodes 12 and 14 may comprise a polyimide film such as the KAPTON polyimide film.

The drug delivery system 10 may include an exemplary control circuit 16 that includes a microcontroller 150 programmed to control a current flow between the first electrode 12 and the second electrode 14. The control circuit 16 may include an on/off switch, such as a dome switch. In an exemplary embodiment, the microcontroller 150 may control the electrotransport current by controlling a power supply using a linear regulator. In another exemplary embodiment, the microcontroller 150 may control the power supply using any type of a switching regulator, e.g. pulse width modulation (PWM), pulse frequency modulation (PFM), etc. An exemplary embodiment of the microcontroller 150 is discussed below in relation to FIG. 11.

In an exemplary embodiment, the control circuit 16 may be separable from the first and second electrodes 12 and 14. In this embodiment, the electrodes may be disposed after use and the control circuit 16 may be re-used. In another exemplary embodiment, the control circuit 16 may be integrally attached to the electrodes.

The drug delivery system 10 may also include a first conductive reservoir 30 holding a first conductive medium and a first therapeutic drug or agent and a second conductive reservoir 32 holding a second conductive medium that may contain a second therapeutic drug or agent. In use, current supplied to the first electrode 12 delivers the first therapeutic drug or agent from the first conductive reservoir 30 through a portion of the user's skin in contact with the first conductive reservoir 30. Current returns to the second electrode 14 through a portion of the user's skin in contact with the second conductive reservoir 32. The second therapeutic drug or agent may have a charge opposite that of the first therapeutic drug or agent. Foam rings may be used to hold the conductive drug reservoirs in place. The foam rings may further keep the anode and cathode of the electrodes separated.

A first removable barrier 34 may form a first barrier seal removably disposed between the first electrode 12 and the first conductive reservoir 30. A second removable barrier 36 may form a second barrier seal removably disposed between the second electrode 14 and the second conductive reservoir 32. Alternatively, the first removable barrier 34 may form both the first barrier seal and a second barrier seal removably disposed between the second electrode 14 and the second conductive reservoir 32. In an exemplary embodiment, the first removable barrier 34 may include foil. Prolonged contact between the first conductive reservoir 30 including the therapeutic agent 46 and the first electrode 12 may cause degradation of the first electrode 12, the therapeutic agent or both. The first removable barrier 34, which forms the first barrier seal, may prevent the first conductive reservoir 30 including the therapeutic agent 46 from coming into contact with the first electrode 12, thus preventing water transmission. By separating the first conductive reservoir 30 from the first electrode 12 with a sealed barrier ("sealingly separating") and sealingly separating the second conductive reservoir 32 from the second electrode 14, the drug delivery system 10 maintains efficacy and reliability, thus providing a longer shelf-life.

The drug delivery system 10 may also include a housing 38 to house the first electrode 12, the second electrode 14, the control circuit 16, the first conductive reservoir 30 and the second conductive reservoir 32. The housing 38 has a top housing portion 38a that is coupleable to a bottom housing portion 38b. The top housing portion 38a and the bottom housing portion 38b are coupled to form a slotted sidewall portion 40a through which the first removable barrier 34 extends. Similarly, the top housing portion 38a and the bottom housing portion 38b may form a second slotted sidewall portion 40b through which the second removable barrier 36 extends. The portion of the first removable barrier 34 that extends outside the housing 38 provides a user access to the first removable barrier 34 without opening the housing. The removable barrier 34 is configured to be removed while the first electrode 12, the second electrode 14, the control circuit 16, the first conductive reservoir 30 and the second conductive reservoir 32 remain within the housing. The portion of the first removable barrier 34 extending through the slotted sidewall portion 40a may be in the form of a first tab 34a. Likewise, a portion of the second removable barrier 36 extending through the second slotted sidewall portion 40b may be in the form of a second tab 36a.

A user may remove the first removable bather 34 and the second removable barrier 36 by pulling on the first tab 34a and the second tab 36a, respectively, without accessing the first electrode 12, the second electrode 14, the control circuit 16, the first conductive reservoir 30 and the second conductive reservoir 32, enabling assembly of a self-contained iontophoretic drug delivery system while components of the self-contained iontophoretic drug delivery system remain within the housing 38.

Figure 3:
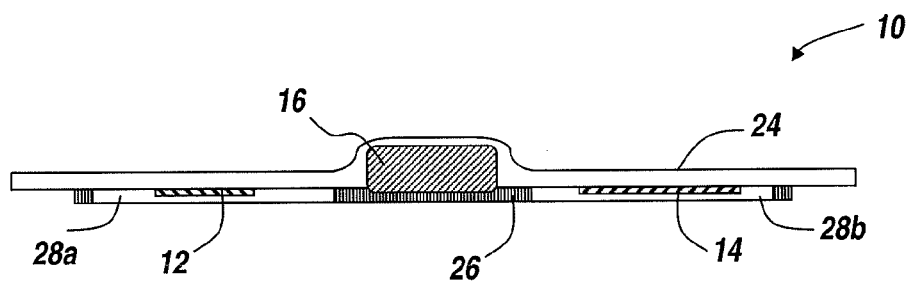
FIG. 3 depicts a cross-sectional side view of a portion of an exemplary iontophoretic drug delivery system that includes a first electrode, a second electrode and a controller.
Figure 4:
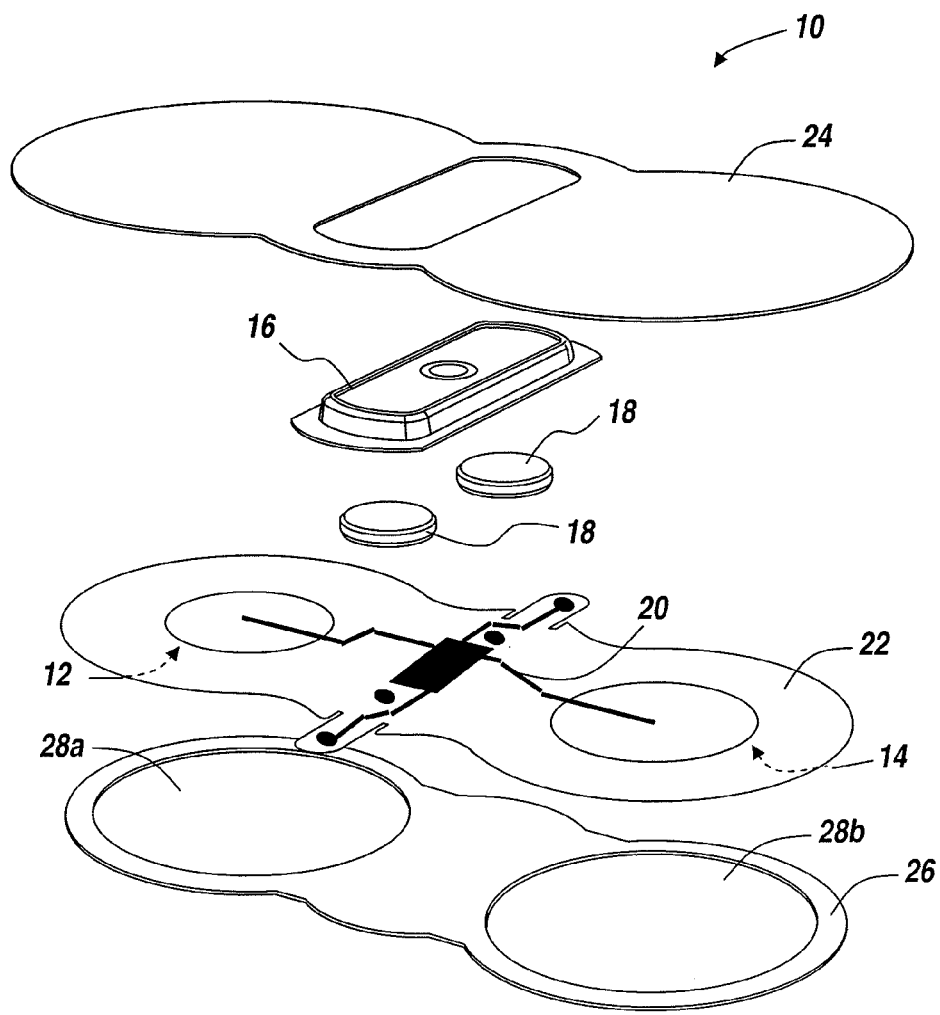
FIG. 4 depicts an exploded perspective view of the portion depicted in FIG. 3.

FIGS. 3 and 4 depict a portion of the exemplary self-contained iontophoretic drug delivery system 10 that includes the first electrode 12, the second electrode 14 and the control circuit 16. In the side cross-sectional view depicted in FIG. 3, some thicknesses are exaggerated for illustrative purposes.

The first electrode 12 and the second electrode 14 may be described as an electrode region of the drug delivery system 10. The drug delivery system 10 may include at least one battery 18 for providing current to the control circuit 16, the first electrode 12 and the second electrode 14. The control circuit 16 may be electrically connected to at least one battery 18, the first electrode 12 and the second electrode 14 with circuitry 20. The circuitry 20, the first electrode 12 and the second electrode 14 may be disposed on an electrode support layer 22.

The control circuit 16, the first electrode 12 and the second electrode 14 may be supported by a backing layer 24. The electrode support layer 22 may be affixed to the backing layer 24.

The drug delivery system 10 may also include a receiving layer 26 that has a first recess 28a configured to receive the first conductive reservoir 30 and a second recess 28b configured to receive the second conductive reservoir 32.

The current controlled by the control circuit 16 may transdermally deliver the drug to the user. Iontophoretic transport of the drug is heavily influenced by the current density of the treatment electrode. Thus, the current profile in time may be adjusted to achieve a desired profile of drug delivery, i.e. the profile of drug concentration (e.g., in the plasma) versus time during the total dosing period.

The control circuit 16 may use a configurable microprocessor, a programmable microprocessor, a programmable microcontroller, a configurable microcontroller or a microprocessor that is both configurable and programmable to set or adjust a desired current profile in time. The total dosing period may be adjusted based on a single factor or a combination of factors. Some factors may include, but are not limited to, the life of the power supply of the system 10, the total amount of the drug to be delivered, user age, user weight, type of drug, user health, drug delivery protocol, and other like factors. Alternatively, the total dosing period may be set to any time period, e.g. hours, days, or weeks. For example, the total dosing period may be set to a few hours during which high concentrations of a drug are released, or the total dosing period may be set to a few weeks during which sustained, low concentrations of a drug are released.

In an exemplary embodiment, the drug delivery system 10 may adjust the drug delivery profile by adjusting the electrotransport current profile, based on the quantity and/or one or more characteristics of the drug to be delivered. In an exemplary embodiment, the drug delivery system 10 may adjust the drug delivery profile, by adjusting the electrotransport current profile, based on one or more characteristics of the user, e.g. the user's weight, age, health, skin resistance, etc. The electrotransport current profile may also be adaptive to yet other parameters. For example, the system may include one or more sensors for measuring the concentration of the drug in the user's system (e.g. the user's blood), and the electrotransport current profile may be adaptive to the concentration of the drug in the user's system.

In an exemplary embodiment, the microcontroller 150 may be programmed with a drug delivery profile at the site of manufacture of the drug delivery system 10. In another exemplary embodiment, the microcontroller 150 may be programmed or re-programmed with a delivery profile at the pharmacy subsequent to the manufacture of the drug delivery system 10. In this embodiment, a pharmacist may program or re-program the microcontroller 150 to achieve a desired drug delivery profile based on the drug, (e.g. drug concentration, dosage volume, etc) and/or the user (e.g. user size, age, etc). The programming or re-programming of the microcontroller 150 may adjust one or more aspects of the drug delivery profile, e.g. the rate of drug delivery, the concentrations of drug delivery, etc.

The microcontroller 150 of the drug delivery system 10 may be programmed to drive current of a predetermined profile into the user's skin. The current profile may not be limited to a particular shape, and may include one or more square waves, sine waves, ramps, arbitrary shapes, or any combination of waveforms, etc.

FIGS. 1-4 depict exemplary embodiments of a drug delivery system (i.e., a "patch") having a certain packaging configuration. Other exemplary embodiments of a drug delivery system as taught herein may have different packaging configurations as taught, for example, in U.S. Pat. No. 6,745,071 to Anderson et al., entitled "Iontophoretic Drug Delivery System" or in U.S. patent application Ser. No. 12/181,142 to Anderson et al. published as US Patent Publication No. 2008/0287497 on Nov. 20, 2008, entitled "TRANSDERMAL METHODS AND SYSTEMS FOR THE DELIVERY OF ANTI-MIGRAINE COMPOUNDS." U.S. Pat. No. 6,745,071 and US Patent Publication No. 2008/0287497 are incorporated herein by reference in their entirety.

Figure 5:
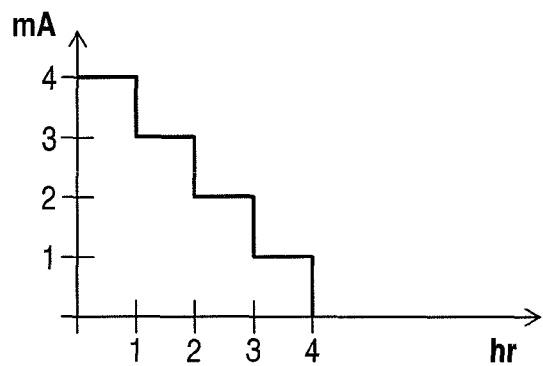
FIGS. 5-8 depict exemplary current profiles achievable by an exemplary controller of an exemplary drug delivery system taught herein.
Figure 6:
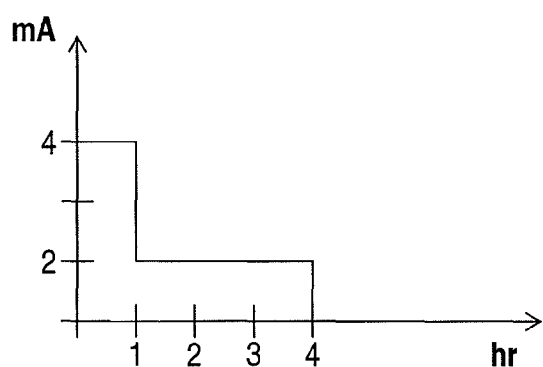
Figure 7:
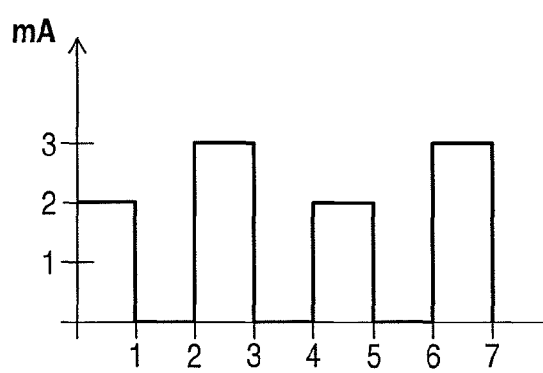
Figure 8:
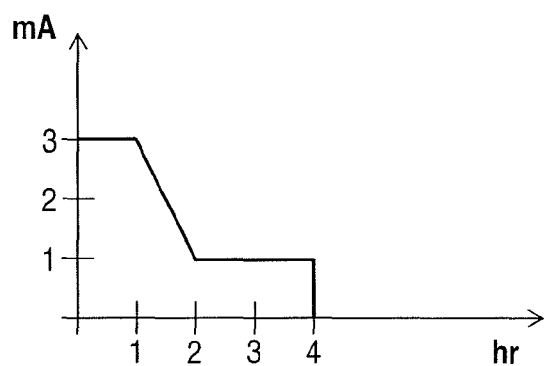

FIGS. 5-8 depict exemplary current profiles achievable by the microcontroller 150, where the current is plotted versus time and where the current is constant, increasing or decreasing. In FIG. 5, an electrotransport current is administered for a total dosing period of 4 hours. The current is held at 4 mA for the first hour, at 3 mA for the second hour, at 2 mA for the third hour, and at 1 mA for the fourth hour. In FIG. 6, the current is held at 4 mA for the first hour, and at 2 mA for the next three hours. In FIG. 7, the current is held at 2 mA for the first and fifth hours, at 0 mA for the second, fourth and sixth hours, and at 3 mA for the third and seventh hours. In FIG. 8, the current is held at 3 mA for the first hour, ramped down to 1 mA during the second hour, and held at 1 mA for the third and fourth hours.

The microcontroller 150 may be programmed to achieve a first set of current levels to be applied during the day and a second set of current levels to be applied during the night.

Figure 9:
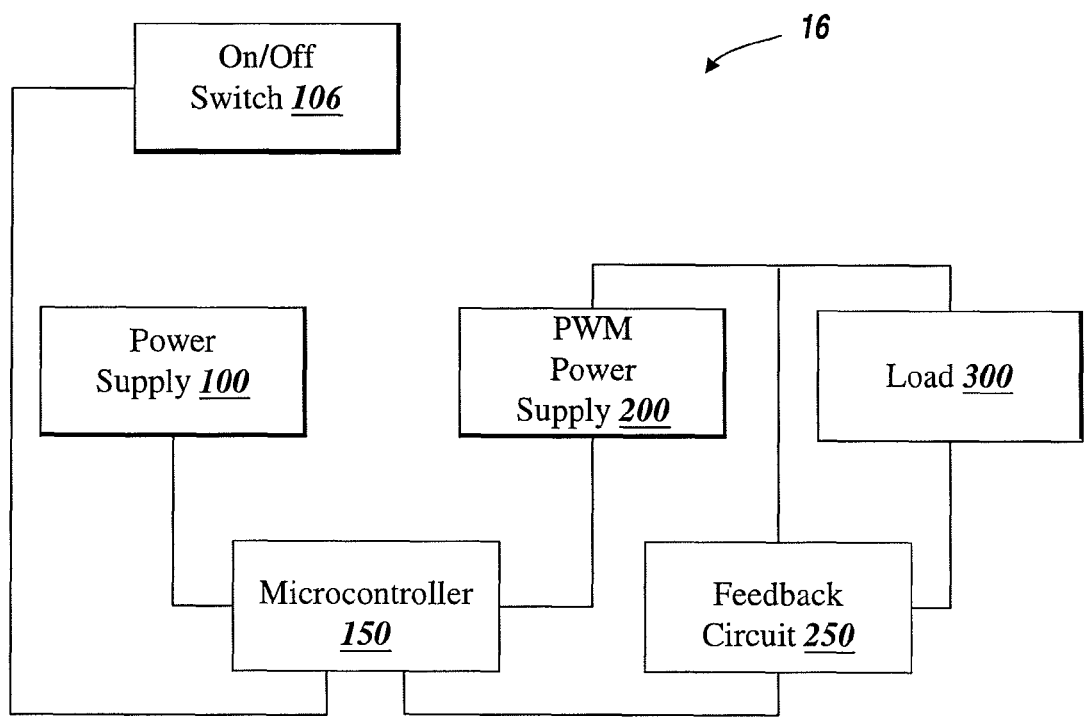
FIG. 9 depicts a general block diagram of an exemplary electronic circuit for controlling an exemplary drug delivery system taught herein.

FIG. 9 depicts a block diagram of an exemplary electronic control circuit 16 for controlling the drug delivery system 10. The electronic control circuit 16 may include a switch 106 connected to a microcontroller 150. The microcontroller 150 may also be connected to a power supply 100 and a controllable power supply 200. The controllable power supply 200 may be connected to a load 300 to drive an electrotransport current through the load 300. A feedback circuit 250 may be connected to the load 300, the controllable power supply 200 and the microcontroller 150. The electronic control circuit 16 is implementable on a flexible circuit (e.g. copper on the KAPTON polyimide film, a printed circuit board or both.

The power supply 100 may provide electrical energy to the circuit. The microcontroller 150 may be programmed to control the controllable power supply 200.

The controllable power supply 200 may increase, decrease or maintain the output voltage of the power supply 100 to control load current ($I_L$) across load 300. In an exemplary embodiment, the microcontroller 150 may use a linear regulator to control the controllable power supply 200. In another exemplary embodiment, the microcontroller 150 may use any type of a switching regulator to control the controllable power supply 200, e.g. pulse width modulation (PWM), pulse frequency modulation (PFM), etc. In an embodiment that employs PWM, the microcontroller 150 may employ pulse width modulation, i.e. control a duty cycle and pulse width, to control or adjust the load current ($I_L$).

The load 300 may include the user's skin, through which a drug is delivered when the load current is driven across the load 300.

The feedback circuit 250 may allow the microcontroller 150 to detect the load current flowing across the load 300 and the output voltage at the load 300. This allows the microcontroller 150 to monitor and perform current correction, i.e. to adjust the load current flowing across the load 300. This also allows the microcontroller 150 to monitor and control the voltage level generated by the controllable power supply 200.

In an embodiment that employs a pulse width modulation (PWM) controllable power supply 200, the microcontroller 150 may generate time-based interrupts and send time-based signals to toggle a switch on/off at the PWM controllable power supply 200. The duty cycle of the PWM controllable power supply 200 is the proportion of time the switch at the PWM is turned on. In order to perform current correction, the microcontroller 150 may turn the PWM switch off, compare the load current ($I_L$) to a dynamic value representative of the target load current value, and adjust the duty cycle of the PWM controllable power supply 200 based on a result of the comparison. The microcontroller 150 may adjust the duty cycle by changing the frequency and/or the duration of the time-based signals which toggle the switch on/off at the PWM controllable power supply 200. By adjusting the load current in this manner, the microcontroller 150 may be able to achieve a load current profile that is desirable for delivery of the drug to the user's body.

In some embodiments, the exemplary circuit 900 may be capable of driving an electrotransport load current ($I_L$) at voltages ranging from 0.4-12 V±10%. In some embodiments, the exemplary control circuit 16 may be capable of driving an electrotransport load current ($I_L$) at voltages ranging from 0.4-12 V±10%. In some embodiments, the system resistances may be in the range of 200-5,000 Ohms. In some embodiments, the system resistances may be in the range of 100-6,000 Ohms. The exemplary control circuit 16 may be capable of providing a maximum output voltage of 12 V to drive an electrotransport load current of 4 mA for resistances of up to 3,000 Ohms. However, in an exemplary embodiment, the control circuit 16 may only provide 10-12 V for up to five minutes during the first 60 minutes of operation. This five-minute limit on the higher voltages preserves the battery power.

Figure 10:
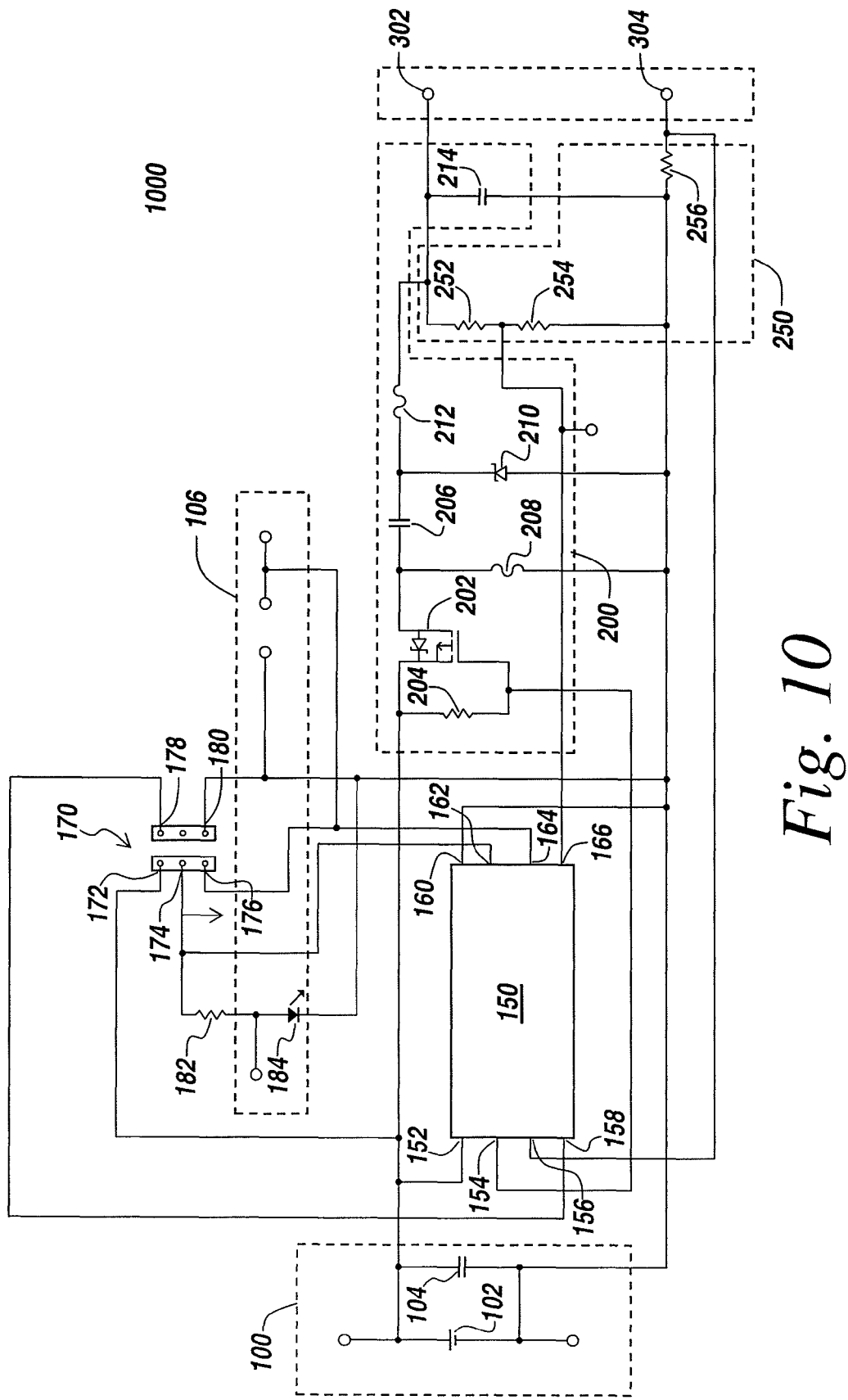
FIG. 10 depicts a schematic of an exemplary electronic circuit for controlling an exemplary drug delivery system taught herein.

FIG. 10 depicts a schematic representation of a suitable electronic circuit 1000 for administering a therapeutic agent or drug. The electronic circuit 1000 is one exemplary embodiment of exemplary circuit 16.

The system may include a power supply 100 which may include one or more power sources 102 connected in series or parallel. The number and connection of power sources, for example, one or more batteries may be determined based on the power requirements for the delivery of a drug and the total duration of the circuit's operation. The power supply 100 may also include one or more capacitors 104 connected in parallel with the power source 102.

In one embodiment, the power supply 100 may be integrated with the other components of the drug delivery system 10. In another embodiment, the power supply 100 may be provided separately from the other components of the drug delivery system 10.

The system may include a switch 106 which may be closed to activate the system. In an exemplary embodiment, the switch 106 may be a momentary switch, e.g. a button or slider, which may be used to activate the microcontroller 150. In another exemplary embodiment, the switch 106 may be an on/off switch which may be toggled on/off to activate or deactivate the microcontroller 150.

The system may also include an on/off indicator, for example, an LED 184 connected in series with a resistor 182 if necessary or desirable given the operating parameters of the indicator. In an exemplary embodiment, the LED 184 may turn on, turn off or blink to indicate to a user the present mode of operation of the system. Moreover, the LED 184 may indicate, e.g., by turning off, when the dosing period has finished. In an exemplary embodiment, the LED 184 may be off when the system is in an Off Mode or an Inactive Mode, blink when the system is in a Test Mode, and be on when the system is in a Run Mode. These exemplary modes will be described in more detail with respect to FIG. 11. In another exemplary embodiment, the system may emit an audio tone alone or in combination with the visual indication to indicate that the system is in a certain mode.

The system may also include an external LCD display which may show the present electrotransport current, the elapsed time and/or the drug delivery profile.

The system may include the microcontroller 150 which may implement a control loop to achieve a desired drug delivery profile. External nodes may be provided in the microcontroller for electrical connection to the other components in the circuit. The main function of the microcontroller 150 is to control the electrotransport load current driven across the load 300. In an exemplary embodiment, the microcontroller 150 may employ a linear regulator to control the electrotransport load current. In another exemplary embodiment, the microcontroller 150 may employ any type of a switching regulator, e.g. pulse width modulation (PWM), pulse frequency modulation (PFM), etc. In an embodiment employing PWM control of the controllable power supply 200, the microcontroller 150 may control the electrotransport load current by either increasing the duty cycle of the PWM controllable power supply 200 or by decreasing the duty cycle of the PWM controllable power supply 200.

In one embodiment, the microcontroller may be a PIC12F615, having an 8-pin package with flash-based 8-bit complementary metal-oxide-semiconductor (CMOS) microcontroller manufactured by Microchip Technology, Inc. A detailed schematic of the PIC12F615 microcontroller can be found in the PIC12F609/615/12HV609/615 data sheet published by Microchip Technology, Inc. in 2008, incorporated herein by reference. In one embodiment, the microcontroller 150 may be pre-programmed, i.e. may contain a program before being placed in the system circuit. In another embodiment, the microcontroller 150 may be programmed after its placement in the system circuit.

In an exemplary embodiment, the microcontroller 150 may be programmed only once. In another exemplary embodiment, the microcontroller 150 may be programmed a first time with a first current profile. The microcontroller 150 may be re-programmed, i.e. programmed a second time, with a second current profile. This re-programming of the microcontroller 150 allows alteration or correction of a current profile, and also allows the same system to be reused for different users and/or different drugs.

The programming of the microcontroller 150 will now be described in detail. In order to program the microcontroller 150, a programmer may generate a program in a suitable format, e.g. in a HEX file, to specify how the non-volatile memory bits of the microcontroller 150 are to be set. The programmer may then use a programming interface 170 to store the program in the microcontroller 150. The programming interface 170 may be connected to an I/O port of a PC (not pictured) on one side and to the microcontroller 150 on the other side. In an exemplary embodiment, the programming interface 170 is an in-circuit programming interface which may connect to the microcontroller 150 while the microcontroller is connected to the system circuit. In this embodiment, program data may be transferred to the microcontroller 150 using a two-wire synchronous serial scheme with a clock controlled by the programming interface 170.

The ground (GND) node 180 of the programming interface 170 may be connected to the negative power input (VSS) at node 160 of the microcontroller 150. The positive power input (VDD) node 172 of the programming interface 170 may be connected to the positive power input (VDD) at node 152 of the microcontroller 150. The programming voltage (MCRL) node 178 of the programming interface 170 may be connected to the programming mode voltage at node 158 of the microcontroller 150. To put the microcontroller 150 into the programming mode, this MCRL line must be in a specified range above the VDD line. The programming clock (PGC) node 176 of the programming interface 170 is the clock line of the serial data interface and may be connected to node 164 of the microcontroller 150. The voltage at the PGC node 176 swings from GND to VDD, and data is transferred on the falling edge. The programming data (PGD) node 174 of the programming interface 170 is the serial data line and may be connected to node 162 of the microcontroller 150. The voltage at the PGD node 174 swings from GND to VDD.

The connections of the external nodes of the microcontroller 150 will now be listed. Node 152 is the positive power input (VDD) to the microcontroller 150, and may be connected to the power supply 100. Node 154 is an output node coupled to a switch of the controllable power supply 200 to allow the microcontroller 150 to control the operation of the controllable power supply 200. The node 154 may be connected to the gate of a switch 202. In an exemplary embodiment, the switch 202 may be a p-channel metal-oxide-semiconductor field-effect transistor (MOSFET) 202. Node 156 may be connected to the positive terminal of the sense resistor 256. Node 158 may be connected to the MCRL node 178 of the programming interface 170. Node 160 is the negative power input to the microcontroller 150 and may be connected to the negative terminal of the sense resistor 256 to allow the microcontroller 150 to monitor the load current ($I_L$) across the load 300. Node 162 may be connected to the PGD node 174 of the programming interface 170. Node 164 may be connected to the external switch 106 of the system. Node 166 may be connected to the voltage divider created by resistors 252 and 254 to allow the microcontroller 150 to monitor the voltage generated by the controllable power supply 200.

In an exemplary embodiment (not depicted in FIG. 10), the controllable power supply 200 may be configured as a buck-boost converter which allows the output voltage at the load 300 to be higher or lower than the power source 102 voltage. The "boost" stage refers to output voltages above the power source 102 voltages, and the "buck" stage refers to output voltages below the power source 102 voltage.

In another exemplary embodiment (depicted in FIG. 10 and described further below), the controllable power supply 200 may include a standard inverse single-ended primary inductor converter (SEPIC). In this embodiment, the controllable power supply 200 may include a resistor 204 which has a positive terminal connected to the positive terminal of the power source 102 and a negative terminal connected to the node 154 of the microcontroller 150. The controllable power supply 200 may also include a switch 202 which has a gate connected to the node 154 of the microcontroller 150, a source connected to the positive terminal of the power source 102, and a drain connected to a positive terminal of the first inductor 208 and a positive terminal of the first capacitor 206. The resistor 204 and the switch 202 in the controllable power supply 200 may work in conjunction with the microcontroller 150 to act like a switch and gate the power supply voltage into a first inductor 208.

The controllable power supply 200 may include the first inductor 208 which has a first terminal connected to the drain of the switch 202 and a first terminal of the first capacitor 206. The first inductor 208 may have a second terminal connected to the negative terminal of the power source 102. The controllable power supply 200 may include a first capacitor 206 which has a first terminal connected to the first terminal of the first inductor 208 and to the drain of the switch 202. The first capacitor 206 may have a second terminal connected to a second terminal of a second inductor 212 and to a first terminal of a Schottky diode 210.

The controllable power supply 200 may include the Schottky diode 210 which has a first terminal connected to the first terminal of the first capacitor 206 and the second terminal of the second inductor 212. The Schottky diode 210 has a second terminal connected to the negative terminal of the power source 102. The controllable power supply 200 may include a second inductor 212 which has a first terminal connected to the second terminal of the first capacitor 206 and to the first terminal of the Schottky diode 210. The second inductor 212 has a second terminal connected to a voltage divider and to a first terminal of a second capacitor 214. The controllable powers supply 200 may include the second capacitor 214 which has a first terminal connected to the voltage divider and the second terminal of the second inductor 212. The second capacitor 214 has a second terminal connected to the negative terminal of the power source 102.

The load 300 may be coupled between the first electrode 302 and the second electrode 304 which may be applied to the user's skin.

The feedback circuit 250 may include a voltage divider formed by a first resistor 252 and a second resistor 254. The first resistor 252 may have a first terminal connected to the second terminal of the second inductor 212 and to the first terminal of the second capacitor 214. The first resistor 252 may have a second terminal connected to the first terminal of the second resistor 254. The second resistor 254 may have a second terminal connected to the negative terminal of the power source 102. The voltage divider allows the microcontroller 150 to monitor and control the voltage generated by the controllable power supply 200. The feedback circuit 250 may also include a sense resistor 256 which may be used to detect the electrotransport current flowing between the electrodes 302 and 304.

Figure 11:
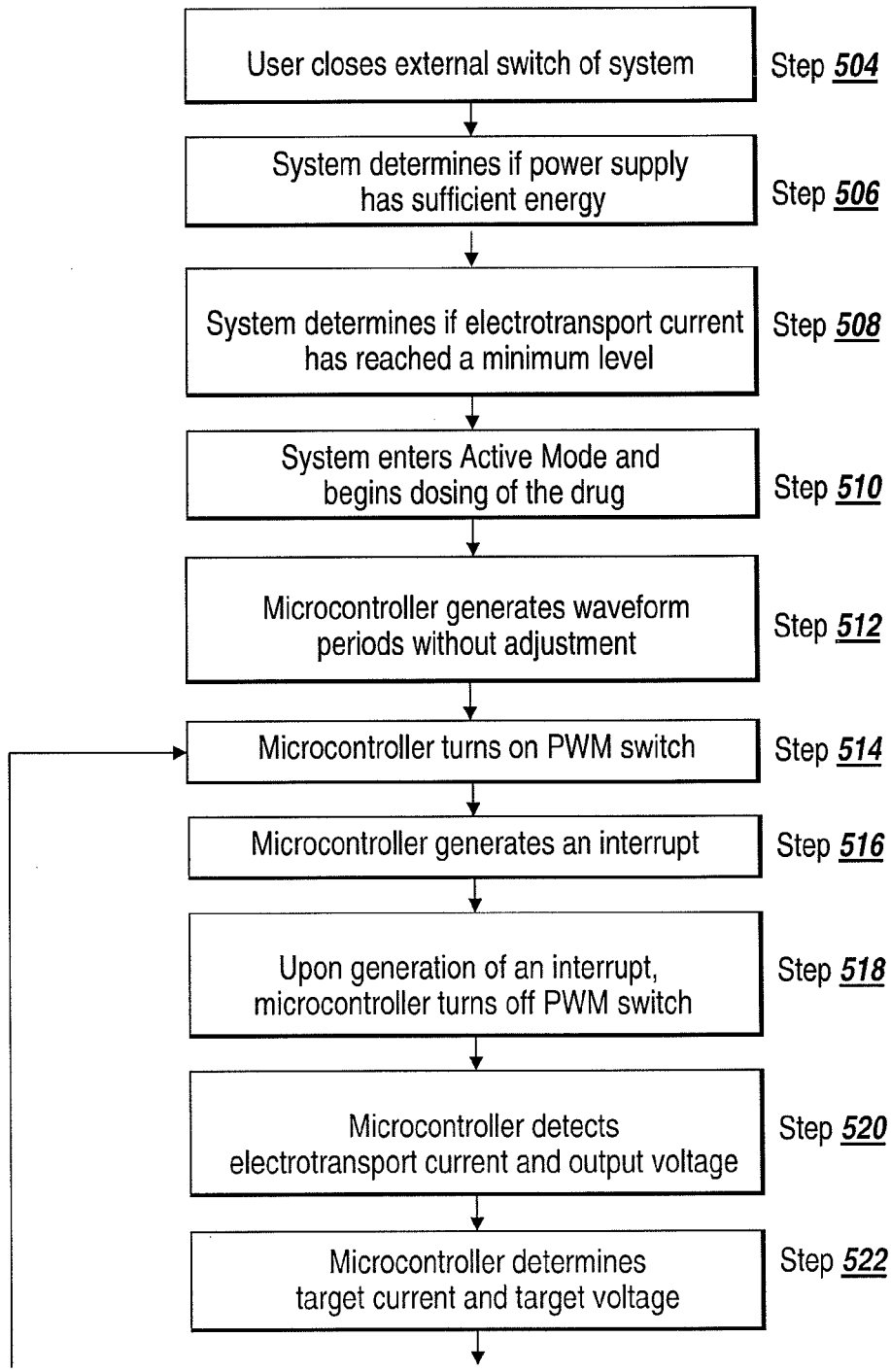
FIG. 11 depicts a flow diagram of an exemplary control loop implemented by the exemplary electronic circuit depicted in FIG. 10.

Operation of the exemplary circuit 1000 will now be described in relation to FIG. 11. FIG. 11 depicts a flow diagram of an exemplary control loop implemented by the exemplary electronic circuit depicted in FIG. 10.

The exemplary circuit 1000 is described with reference to a pulse width modulation (PWM) power supply 200, i.e. a controllable power supply 200 controlled by the PWM. Nonetheless, the present invention is not meant to be limited to this particular embodiment of a controllable power supply 200. Exemplary embodiments may also employ other types of controllable power supplies 200, e.g. a linear regulator-controlled power supply, any type of a switching regulator-controlled power supply, etc.

The system may be kept in an Off Mode from the time the device is assembled until a user activates the external switch 106 to turn on the system. In the Off Mode, the microcontroller 150 may perform some minimal operations, e.g. detect activation of the system by a user using the external switch 106. While in the Off Mode, the system may provide a visual or auditory indication that the system is in the Off Mode and has not yet been activated. In an exemplary embodiment, the LED 184 may be off during the Off Mode.

In step 504, the user may close the external switch 106 to turn on the system. To prevent accidental activation of the system, in an exemplary embodiment, the user may need to press on the switch for a minimum period of time, e.g. 1 second, to turn on the system.

Upon closing of the external switch 106, the system may enter a Test Mode before beginning a dosing mode for dosing of the drug. An exemplary Test Mode is described with reference to steps 506 and 508. When in the Test Mode, the system may provide a visual or auditory indication that the system is in the Test Mode. In an exemplary embodiment, the LED 184 may blink during the Test Mode.

In step 506, before beginning dosing of the drug, the microcontroller 150 may determine if the power supply 100 has sufficient stored electrical energy to complete the full dosage protocol of the drug. In some circumstances, the stored energy of the power supply 100 may become depleted even before use, e.g. if the power supply is defective, run down and/or was accidentally turned on numerous times during handling. It may be risky to initiate drug delivery with such a depleted power supply, because the user may receive a less than intended dosage if the power supply runs out before the end of the full dosing period.

To prevent the user from operating the system with a depleted power supply, in step 506, the microcontroller 150 may detect the voltage of the power supply 100 at node 152, and determine if this voltage is above a minimum threshold voltage. This minimum threshold voltage may be the power supply voltage required to deliver the total dosage of the drug. If the power supply voltage is determined to be lower than the minimum threshold voltage, then the system may not be activated and may enter an Inactive Mode. The output current of the system during the Inactive Mode may be less than 10 μA, which does not deliver any significant amount of the drug. The system may provide a visual or auditory indication that the system is in the Inactive Mode. In an exemplary embodiment, the LED 184 may be off during the Inactive Mode.

In one embodiment, the power supply 100 may be provided separately from the system circuitry. In this case, the user may replace the old power supply 100 with a new power supply, and re-activate the system.

In step 506, if the power supply voltage is determined to be equal to or higher than the minimum threshold voltage, then the control loop may advance to step 508.

In some circumstances, the user may mistakenly press the switch 106 before applying the drug delivery system to his/her body. To prevent dosing from beginning in such circumstances, the microcontroller 150 may start dosing of the drug only after the electrotransport current reaches a minimum level. In step 508, the microcontroller 150 may determine if the electrotransport current has reached a minimum level, e.g. 1 mA, and may begin dosing according to the programmed current profile only after this minimum level is reached. However, if the electrotransport current does not reach the minimum level within a certain time of activation of the switch 106, e.g. 5 minutes during which time the LED 184 flashes, then the system circuit may not be activated and the system may enter the Inactive Mode. The system circuit may later be restarted.

In step 510, the system may enter a Run Mode and may begin dosing of the drug according to the electrotransport current profile programmed in the microcontroller 150. The system may provide a visual or auditory indication that the system is in the Run Mode. In an exemplary embodiment, the LED 184 may be on to indicate that the system is in the Run Mode. The system may monitor the time elapsed since entering the Run Mode.

When an electrotransport current is first applied to the user's skin, the skin resistance tends to be high and gradually decreases as the current continues to be applied. In step 512, immediately after entering the Run Mode, the microcontroller 150 may first output a predetermined PWM waveform for 10 msec before any adjustments are made to the waveform to account for skin resistance. In an exemplary embodiment, the microcontroller 150 may be programmed to measure the user's skin resistance, and determine the time period required in step 512 during which no adjustments are made to the PWM waveform to account for skin resistance.

In step 514, the PWM power supply 200 may operate in its "on" stage. During steps 516-528, the PWM power supply 200 may operate in its "off" stage. The operation of the PWM power supply 200 will now be described in more detail.

The switch 202 and the resistor 204 may work in conjunction with the microcontroller 150 to gate the power supply voltage into the inductor 208. The gating of the power supply voltage into the inductor 208 may control the amount of load current through the load 300. The microcontroller 150 may control the electrotransport current by adjusting the duty cycle of the PWM power supply 200, i.e. by adjusting the proportion of time that the switch 202 is "on."

During the "on" stage of the PWM power supply 200, node 154 of the microcontroller 150 may apply a voltage at the gate of the switch 202 to close the switch 202. Closing the switch 202 may direct the power source 102 voltage into the inductor 208, which also adds to the voltage across the capacitor 206.

During the "off" stage of the PWM power supply 200, node 154 of the microcontroller 150 may turn off the voltage at the gate of the switch 202 to open the switch 202. When the switch 202 opens, electrical energy stored in the magnetic field around the inductor 208 may keep current flowing through the inductor 208 by forcing the Schottky diode 210 to act as a "free wheeling diode." This may continue to drive current through the inductor 212. The current through the inductor 212 may divide between supplying the voltage divider, charging the capacitor 214, and supplying the electrodes 302 and 304.

The operating frequency of the system may vary depending on the load resistance. In an exemplary embodiment, the system may operate at about 156 kHz for high load resistances and at about 78 kHz for low load resistances. This variation in operating frequencies overcomes any hardware-imposed limitations on the minimum "on" time of the PWM power supply 200.

During normal operation, the system may monitor the electrotransport current through the electrodes, and compares the detected electrotransport current to a dynamic value representative of the target current. Based on this comparison, the system may increase or decrease the electrotransport current by controlling the duty cycle of the PWM power supply 200 described above. The duty cycle of the PWM power supply 200 described above is the proportion of time the switch 202 is in the "on" state. In exemplary embodiments, the microcontroller 150 may adjust the duty cycle by changing the frequency and/or the duration of the time-based signals which turn on/off the switch 202.

In step 516, a timer in the microcontroller 150 may generate one or more interrupts at intervals, e.g. at 10 msec intervals. The interrupts may be generated by a timer function in the microcontroller 150. The microcontroller 150 may have a clock oscillator. In an exemplary embodiment, the clock oscillator may run at 8 MHz and may be specified to an accuracy of ±2%. The timer function may count the number of microcontroller clock cycles, and compare the timer value with a fixed number representing the desired time. In an exemplary embodiment, the timer may run on the main clock, e.g. at 8 MHz, and may generate interrupts at 10 millisecond intervals.

The second capacitor 214 may maintain the output voltage and current flow, and thereby valid readings in the circuit.

In step 518, upon the generation of each interrupt, the microcontroller 150 may turn off the switch 202. During the "off" stage of the switch 202, the microcontroller 150 may determine the output voltage applied across the load 300, determine the electrotransport current flowing across the load 300, and a digital representation of an internal bandgap voltage contained in the microcontroller 150. Using these values, the microcontroller 150 may determine if the duty cycle of the PWM power supply 200 needs to be adjusted to set the electrotransport current to a desired level.

In step 520, during the "off" stage of the switch 202, the microcontroller may determine a digital representation of the electrotransport current flowing across the load 300. The electrotransport current may be determined by the voltage drop across the sense resistor 256 which is connected in series with the electrodes 302 and 304. Nodes 156 and 160 of the microcontroller may be connected to the positive and negative terminals, respectively, of the sense resistor 256 to detect the voltage across the sense resistor. An analog-to-digital converter (ADC) in the microcontroller 150 may detect the voltage drop across the sense resistor 256, and determine a digital representation of the electrotransport current by dividing this voltage by the resistance of the sense resistor 256.

The microcontroller may also determine a digital representation of the output voltage applied across the load 300. The output voltage may be determined using the voltage divider composed of resistors 252 and 254. The voltage divider may reduce the detected voltage to a range capable of being processed by the ADC in the microcontroller 150. Node 166 of the microcontroller may be connected between the resistors 252 and 254 of the voltage divider. The ADC in the microcontroller 150 may read the voltage applied across the resistor 254, and determine a digital representation of the output voltage applied across the electrodes based on this voltage.

In an exemplary embodiment, the ADC in the microcontroller 150 may be a 10-bit successive approximation type ADC (1024 counts full scale). The full scale of the ADC is the power source 102 voltage.

In step 522, during the "off" stage of the switch 202, the microcontroller 150 may determine the dynamic value representative of the target current and the dynamic value representative of the target voltage. In an exemplary embodiment, the electrotransport current and output voltage values determined by the microcontroller 150 may first be multiplied by a calibration value which corrects for variability in the bandgap reference.

As described above, the microcontroller 150 may use an ADC to convert measured voltages and currents to their respective digital representations. The ADC may use a reference voltage for conversion purposes which may be supplied by the power supply 100.

Operation of the system circuit may reduce the voltage of the power supply 100 which, in turn, may reduce the reference voltage of the ADC. The microcontroller 150 may account for this gradual reduction in the ADC reference voltage by recalculating the dynamic values and voltage values upon the generation of each interrupt. As the reference voltage decreases, the microcontroller 150 may also perform a reverse correction by expanding its voltage scale to increase the granularity of voltage readings.

In an exemplary embodiment, the dynamic values representative of the target current and the target voltage may then be determined based on the following equations. The electrotransport current (i) used in the following equations may be read from the desired electrotransport current profile programmed in the microcontroller 150. The voltage (v) used in the following equations may be the maximum voltage allowed in the system.

Dynamic value representative of a target electrotransport current of i mA=((Bandgap Voltage×i mA×resistance of the sense resistor 256)/1.20 V reference)×256 bit shift×100.6 nominal reference value Dynamic value representative of a target output voltage of v V=(Bandgap Voltage×v V×1/16 resistor divider)/1.20 V reference)×256 bit shift×100.6 nominal reference value The microcontroller 150 may account for the reduction in the ADC reference voltage by recalculation of the dynamic values representative of the target current and the target voltage upon the generation of each interrupt. Calculation of the dynamic value representative of the target current is based on the target current value, the sense resistor value, the measured bandgap voltage value, a fixed voltage value and a constant. In turn, the digital representation of the current through the sense resistor is compared to the dynamic value representative of the target current to determine if the current through the sense resistor matches the target current value.

In step 524, during the "off" stage of the switch 202, the microcontroller 150 may digitally compare the output voltage with the dynamic value representative of the target voltage, and the electrotransport current with the dynamic value representative of the target current. When driven, the second capacitor 214 has an associated ripple current. During the "off" stage of the switch 202, this ripple current is eliminated.

In step 526, during the "off" stage of the switch 202, if the output voltage is greater than the dynamic value representative of the target voltage, then the microcontroller 150 may decrease the duty cycle of the PWM power supply 200 by one step. This step allows the microcontroller to maintain the output voltage below a certain maximum level irrespective of changes in the resistance of the user's body to avoid burning the user's skin. No current correction is performed in step 526.

In step 528, during the "off" stage of the switch 202, if the output voltage is equal to or less than the dynamic value representative to the target voltage, then the microcontroller 150 may perform current correction in step 530. In step 530, during the "off" stage of the switch 202, the microcontroller 150 may perform current correction based on three conditions outlined in steps 532-536.

If the electrotransport current is greater than the dynamic value representative of the target current, then the microcontroller 150 may decrease the duty cycle of the PWM power supply 200 by one step in step 532. If the electrotransport current is equal to the dynamic value representative to the target current, then the microcontroller 150 may not alter the duty cycle of the PWM power supply 200 in step 534. If the electrotransport current is less than the dynamic value representative of the target current, then the microcontroller 150 may increase the duty cycle of the PWM power supply 200 by one step in step 536.

In addition to the control loop depicted in FIG. 11, the system may monitor the electrotransport current and the output voltage at regular intervals, e.g. 100 Hz. The system may also perform one or more safety tests at regular intervals, e.g. once per second.

If the voltage of the power supply 100 falls below a certain limit during operation, there is a risk that the microcontroller 150 may stop working correctly or shut down. In an exemplary embodiment, the microcontroller 150 may detect this risk by monitoring if the power supply voltage has fallen below a minimum threshold voltage. The minimum threshold voltage may be a voltage below which there is a risk that the microcontroller 150 may stop working correctly or shut down. This minimum threshold voltage may be read off from the datasheet of the microcontroller 150 and adjusted based on the voltage tolerance of the microcontroller. If the power supply voltage is below the minimum threshold voltage, the microcontroller 150 may stop its operation of the system and the system may enter the Inactive Mode. If the power supply voltage is equal to or above the minimum threshold voltage, the system may continue to operate and may remain in the Run Mode.

In an exemplary embodiment, the system may monitor if the electrotransport current is too high (e.g. exceeds 6 mA) for a specified time (e.g. a period exceeding 60 consecutive seconds). In an exemplary embodiment, the system may monitor if the output voltage is too high (e.g. 14 V) for a specified time (e.g. 60 consecutive seconds). In an exemplary embodiment, the system may monitor if the electrotransport current is too low (e.g. remains below 0.2-0.4 mA) for a specified time (e.g. a period exceeding 1 hour). In one embodiment, this specified period (e.g. 1 hour) may be cumulative and may include discontinuous periods of time. In another embodiment, this specified period may be non-cumulative and may only include one continuous period of time. In each case, if the condition is satisfied, the microcontroller 150 may stop operation of the system and the system may enter the Inactive Mode. However, if the condition is not satisfied, the system may continue to operation and may remain in the Run Mode.

In an exemplary embodiment, if the system enters the Inactive Mode due to any of the aforementioned checks, an indicator may be activated to alert the user that the system circuit is in the Inactive Mode. In an exemplary embodiment, this indication may be provided by turning off the LED 184 or emitting an audio tone.

The system may be deactivated at the end of the total dosing period, as determined from the programming of the microcontroller 150. At the end of a successful dosing period, the system may provide a visual or auditory indication that dosing has ended. In an exemplary embodiment, this indication may be provided by turning off the LED 184 or emitting an audio tone.

In an exemplary embodiment, the device is disposable after a single use. In this embodiment, the microcontroller 150 may be programmed to prevent reuse at the end of the total dosing period. At the end of the total dosing period, the microcontroller 150 may be left on to slowly drain the power supply 100. This would eliminate any risk of the device subsequently turning back on. Alternatively, at the end of the total dosing period, the microcontroller 150 may automatically turn on if turned off at the end of the total dosing period to slowly drain the power supply 100

In another exemplary embodiment, the device may be configured for multiple uses. In this embodiment, the microcontroller 150 may be programmed to allow reuse at the end of the dosing period, and the microcontroller 150 will not enter a mode intended to drain the power supply 100 to prevent reuse.

The control loop described above is an incremental control. Such incremental control is appropriate for the drug delivery system because changes on the load presented by the patch will be relatively slow. Chemical changes are likely to take seconds to minutes to cause significant current changes. Even changes due to movement of the patch will occur over hundreds of milliseconds.

In another aspect, the invention provides methods of delivering a therapeutic agent, e.g., sumatriptan succinate, to a user employing any of the drug delivery systems described herein.

In still other aspects, the present invention is directed to methods for treating a user. The method generally includes transdermally administering to the user an effective amount of a drug, wherein the drug is administered using any one of the drug delivery systems used herein.

The drug delivery systems may be applied to any appropriate surface of the user. In some embodiments, the device is applied to the upper arm, leg (e.g., thigh), or back (e.g., upper back). In some embodiments the drug delivery system is worn for a prescribed period of time, e.g., about 1, 2, 3, 4, 5, 6, 7, 8, 9, 10 or more hours. For example, in one embodiment, the drug delivery system includes sumatriptan succinate and is applied to the upper arm or back for about 4 or 5 hours. In another embodiment, the drug delivery system including sumatriptan succinate is applied to the upper arm or back for about 6 hours.

Examples of a therapeutic drug or agent include, but are not limited to an analgesic, anesthetic, anti-arthritis drug, anti-inflammatory drug, anti-migraine drug, cardiovascularly active drug, smoke cessation drug, hormone, non-steroidal anti-inflammatory agent, anti-hypertensive agent, analgesic agent, anti-depressant, antibiotic, anti-cancer agent, local anesthetic, antiemetic, anti-infectant, contraceptive, anti-diabetic agent, steroid, anti-allergy agent, agents for smoking cessation, or anti-obesity agent. Examples of therapeutic drugs or agents include, but are not limited to, nicotine, androgen, estrogen, testosterone, estradiol, nitroglycerin, clonidine, dexamethasone, wintergreen oil, tetracaine, lidocaine, fentanyl, sufentanil, alfentanil, progestrone, insulin, Vitamin A, Vitamin C, Vitamin E, prilocaine, bupivacaine, scopolamine, dihydroergotamine, and pharmaceutically acceptable salts thereof. In a further embodiment, the therapeutic agent is a triptan compound, e.g., sumatriptan, almotriptan, zolmitriptan, rizatriptan, naratriptan, or a combination thereof.

The triptan compound may have a responsive state which is at least one state selected from a group consisting of migraines, familiar hemiplagic migraines (with and without aura), chronic paroxysmal headaches, cluster headaches, migraine headaches, basilar migraines, and atypical headaches accompanied by autonomic symptoms.

In an exemplary embodiment, the therapeutic agent is a triptan compound and the state which is treated is a triptan compound responsive state, e.g., states which can be treated by the administration of a triptan compound. Triptan compound responsive states include almotriptan responsive states, zolmitriptan responsive states, rizatriptan responsive states, sumatriptan responsive states, and naratriptan responsive states. The term also includes migraines, familiar hemiplegic migraines (with and without aura), chronic paroxysmal headaches, cluster headaches, migraine headaches, basilar migraines, and atypical headaches accompanied by autonomic symptoms.

The term "treated," "treating" or "treatment" includes therapeutic and/or prophylactic treatment. The treatment includes the diminishment, alleviation of at least one symptom, or complete eradication of a state or condition.

As taught herein, an exemplary electrode continuity test apparatus may be used for the testing and verification of the function and operation of the electrical connections of the drug delivery system 10 (i.e., iontophoretic drug delivery systems as taught herein). Such exemplary test and verification electrode continuity tester may include an electrode patch continuity test apparatus that is adapted for use in the testing and verification of the electrode connections of the drug delivery system 10.

In certain non-limiting examples, one exemplary electrode continuity test apparatus includes a flat base panel onto which two copper strips are adhered. The copper strips are connected to a switch located inside an enclosure connected to the base panel. A 1 k$\Omega$ resistor is connected in-line with one of the copper strips.

The exemplary electrode continuity test apparatus further includes a top plate having a hole cut in it to permit access to the top of the drug delivery system 10. The top plate is affixed to the base panel. The top plate may be affixed to the base panel by any means known in the art for affixing two layers such that they may be securely layered one on top of the other. For example, the top plate may be affixed to the base panel by a hinge. In certain embodiments, the top plate includes two rubber or foam rings or solid circles that provide pressure to the iontophoretic system when it is placed between the top plate and the base panel and the top plate is closed on top of the base panel. This pressure provides contact between the printed electrodes of the drug delivery system 10 and the copper strips of the base panel. Pressure is maintained by means of a fastening tool which secures the top plate onto the base panel to form a layered structure. For example, the fastening means may be a latch which is attached to the top plate and having a means such that the top plate may be secured to the base panel.

Figure 12:
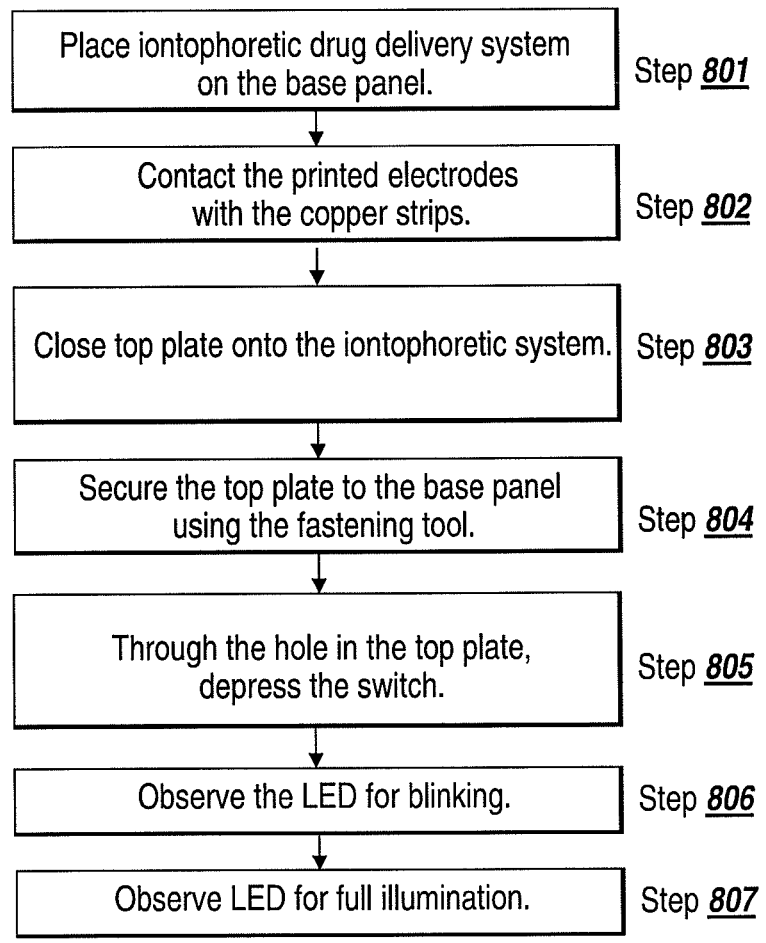
FIG. 12 depicts a flow diagram of an exemplary method of testing the electronic connections of the device such as that depicted in FIG. 1.

FIG. 12 is a block flow diagram depicting an exemplary method for the testing and verification of the electrical connections of the drug delivery system 10. Exemplary methods include the step 801 of placing the drug delivery system 10 on the base panel. In step 802, the printed electrodes are placed in contact with the copper strips of the electrode continuity test apparatus. In step 803, the top plate is closed on top of the drug delivery system 10. In step 804, the top plate is secured to the base panel by the fastening tool. For example, the drug delivery system 10 may be placed on the base panel such that the electrodes of the drug delivery system 10 are placed in contact with the copper strips of the base panel and the top plate is fasted to the base panel forming a layered device wherein the drug delivery system 10 is sandwiched between the base panel and the top plate. The top plate includes a hole therein, whereby access to the control circuit 16 of the drug delivery system 10, as depicted in FIG. 2, is provided. If needed, a power supply is connected to the drug delivery system 10. In step 805, the switch 106 is depressed through the hole in the top plate for about 2-8 seconds. The drug delivery system 10 includes a LED 184 as depicted in FIG. 10. In step 806, the switch 106 is depressed for 2-8 seconds, whereby the LED 184 should blink, indicating that the drug delivery system 10 is in test mode. In step 807, the switch 106 is then pressed and the LED 184 changes to a fully illuminated state. This indicates that the connection between the power supply and the electrode(s) of the drug delivery system 10 are functional.

The electrode continuity test apparatus taught herein provides a rapid functional and operational assessment of the drug delivery system 10. The test apparatus and methods evaluate whether the connections between the electrode and the circuit board assembly of the drug delivery system 10 are compromised, for example damaged due to shipping and handling and processing of the drug delivery system 10.

Exemplary methods may also include methods for testing and measuring the capacity of the electrode of the drug delivery system 10, as taught herein, to deliver a targeted quantity of the drug.

As used herein, the term "capacity" refers to the measurement of the ability of the drug delivery system to delivery a targeted quantity of drug (i.e., over a targeted time interval). Testing and calculation of the capacity ensures that there is enough of the chosen metals to deliver the targeted amount of drug to a subject.

For example, the drug delivery system 10 may include a silver chloride (AgCl) cathode and a zinc (Zn) anode that is used to deliver across the skin of a user an active agent such as, for example, sumatriptan which is a positively charged drug. At the same time, negatively charged ions in the body move away from the silver chloride (AgCl) cathode towards the positive anode. The conductive metal for the electrodes provides the ions that participate in the electrochemical reactions integral to the iontophoretic process.

The quantity and availability of the ions present on the electrode are directly proportional to the ability of the iontophoretic reaction to continue. The electrochemical capacity must be sufficient to support the iontophoretic function of the drug delivery system 10 over the intended time period of use. The target amount of capacity required is determined by factoring into account the total amount of current being provided to the drug delivery system 10 and the total amount of time the drug delivery system 10 is intended to be worn. The electrochemical capacity of an electrochemical cell is limited by the capacity of the anode and cathode electrodes, while operating within their primary electrochemistry. Capacity in this sense is defined as the integral product of applied current and time. Thus the capacity of the drug delivery system 10 cannot exceed that of either the anode or cathode half-cells.

An electrochemical transition between a primary electrochemistry and a secondary electrochemistry can be generalized as a period of relatively constant voltage, followed by an inflection region of high curvature, a relatively steep voltage-time slope, another inflection region with the opposite curvature to the first inflection, and then finally a voltage plateau representing the secondary electrochemistry.

For purposes of the various embodiments of the drug delivery system 10, the capacity is measured at a consistent point in one of the two inflection zones. In the case of the cathode, the primary Ag/Ag—Cl reduction electrochemistry is followed by a secondary reduction electrochemistry of water-splitting, which can cause skin irritation due to creation of a highly basic local environment. For this reason, the cathode transition is defined to occur at the first inflection point. For the anode, the primary zinc oxidation electrochemistry is succeeded by a more benign Ag oxidation electrochemistry. Therefore, the anode endpoint is defined as occurring at the second inflection point.

The method of capacity test, provided herein is achieved by monitoring a controlled current discharge of the Zn anode and the Ag/AgCl cathode pair separated by a dissimilar pair of gel pads identical to those used in the end application. The pad facing the anode consists of polyamine gel containing, for example, 4% by weight of sumatriptan succinate imbibed into a non-woven rayon pad. The present embodiments are exemplary and the drug delivery system 10 contemplates further agents beyond sumatriptan. The cathode-facing pad consists of a gel containing, for example, 0.9% NaCl by weight imbibed into a non-woven rayon pad. The current used during discharge is specified by an exemplary current profile of 4 mA for 1 hour followed by 2 mA for 3 hours with a minimum test duration of about 5 hours, more preferably about 5.5 hours. For example, 1 hour at 4 mA and 4.5 hours at 2 mA. The anode and cathode potentials are monitored during the test with respect to two Ag/AgCl reference electrodes. Electrode capacity in this test is defined by the integrated current-time product measured at the point when a given electrode deviates from its characteristic reaction, as indicated by the measured electrode potential.

Figure 13:
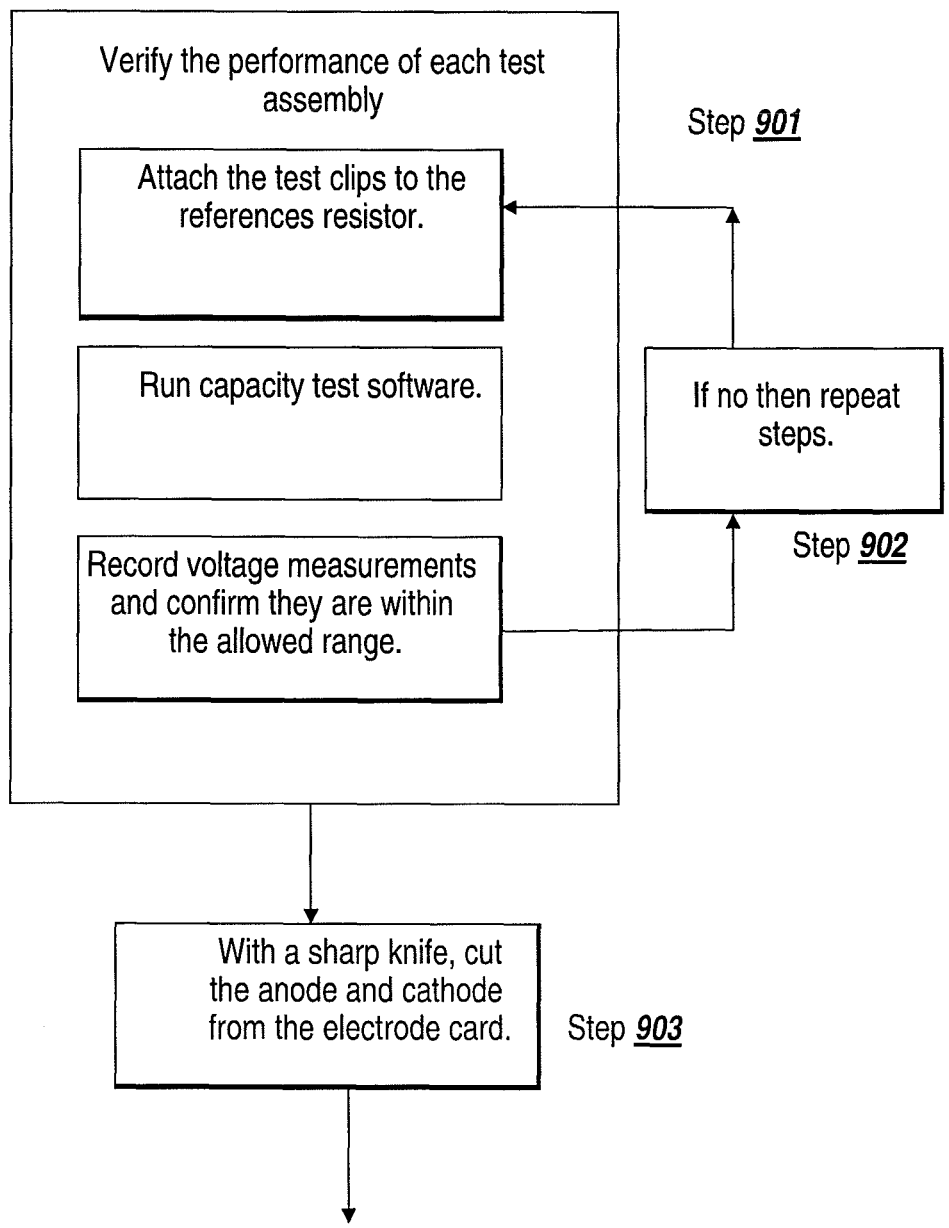
FIG. 13 depicts a flow diagram of an exemplary method of testing the capacity of a device, such as that depicted in FIG. 1, to deliver a target drug quantity.
Figure 13:
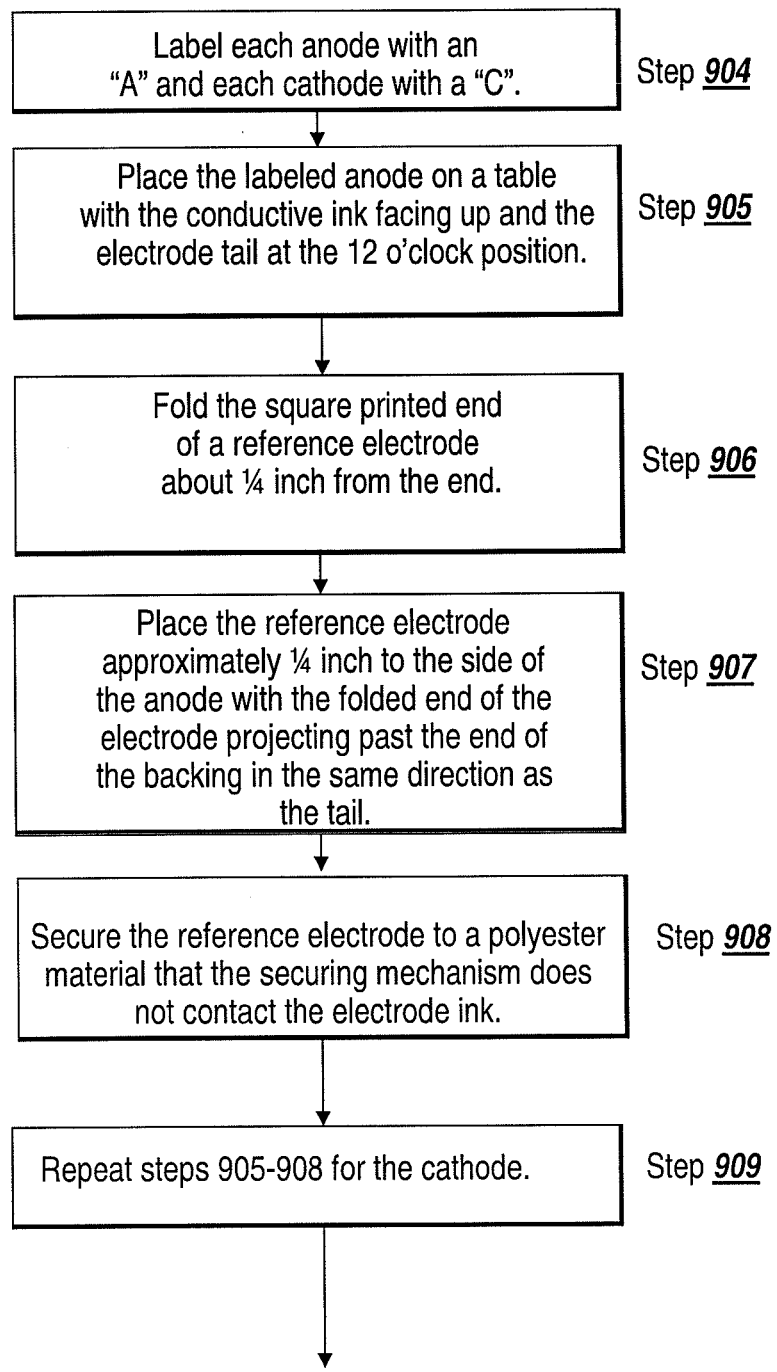
Figure 13:
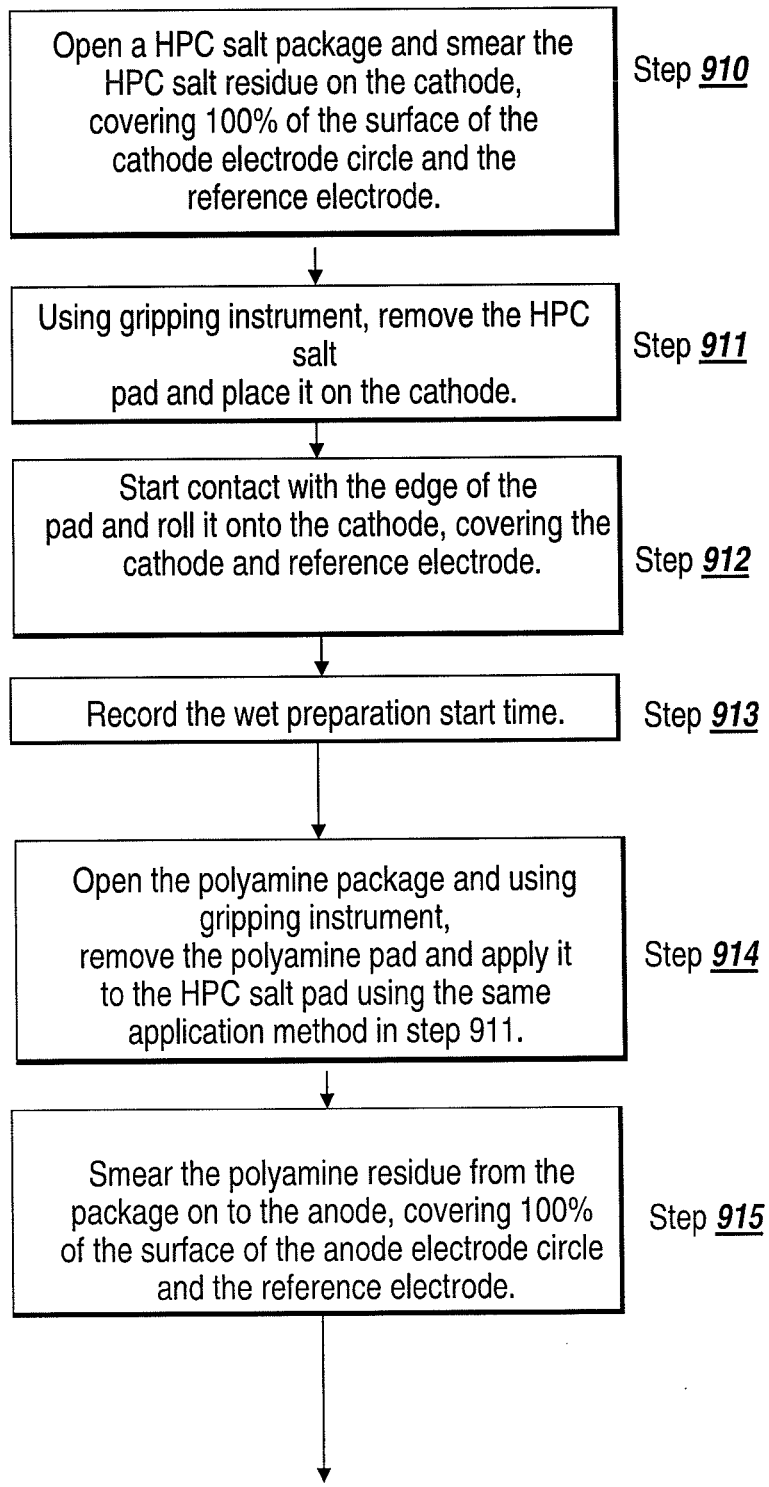
Figure 13:
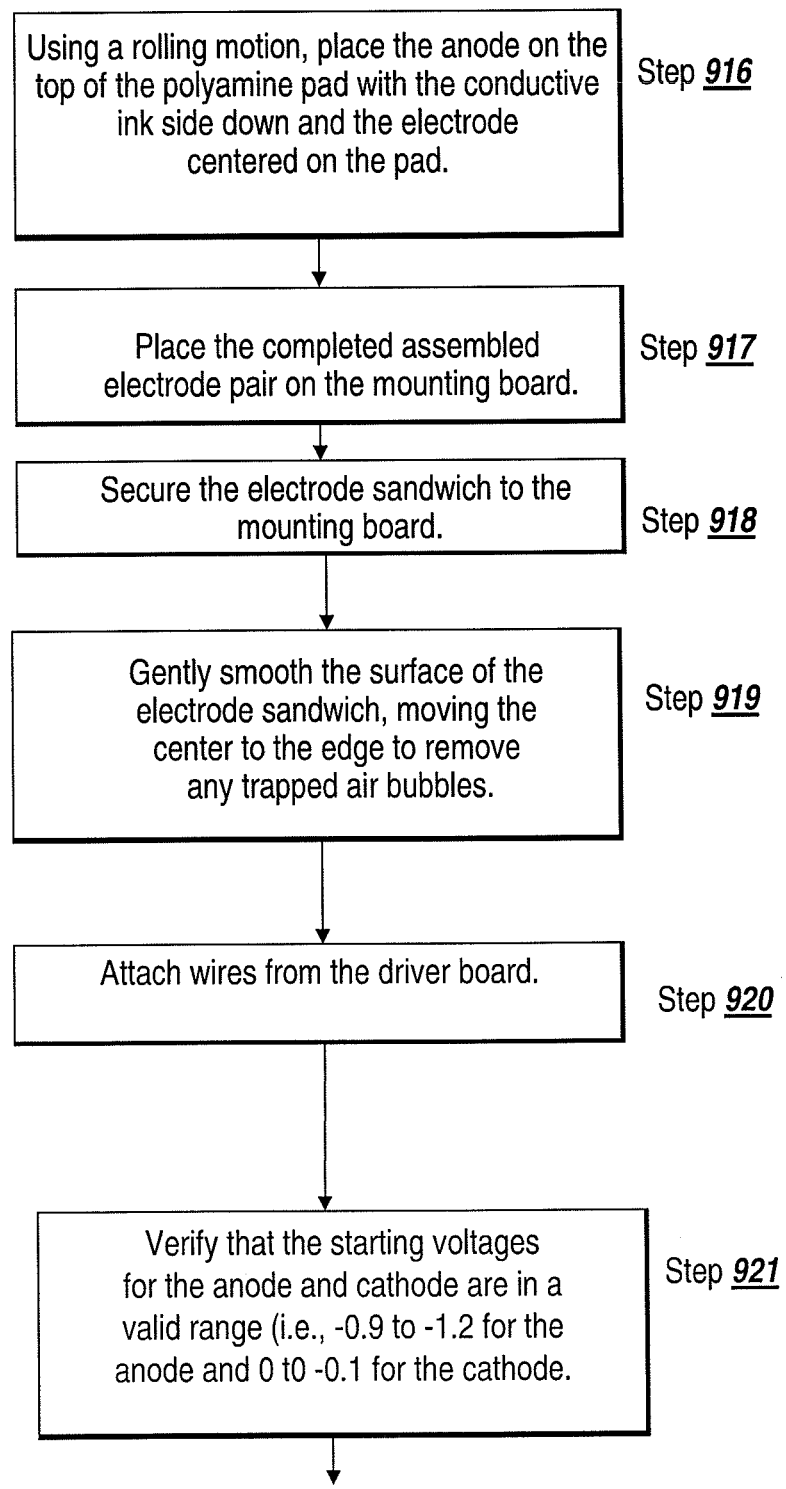
Figure 13:
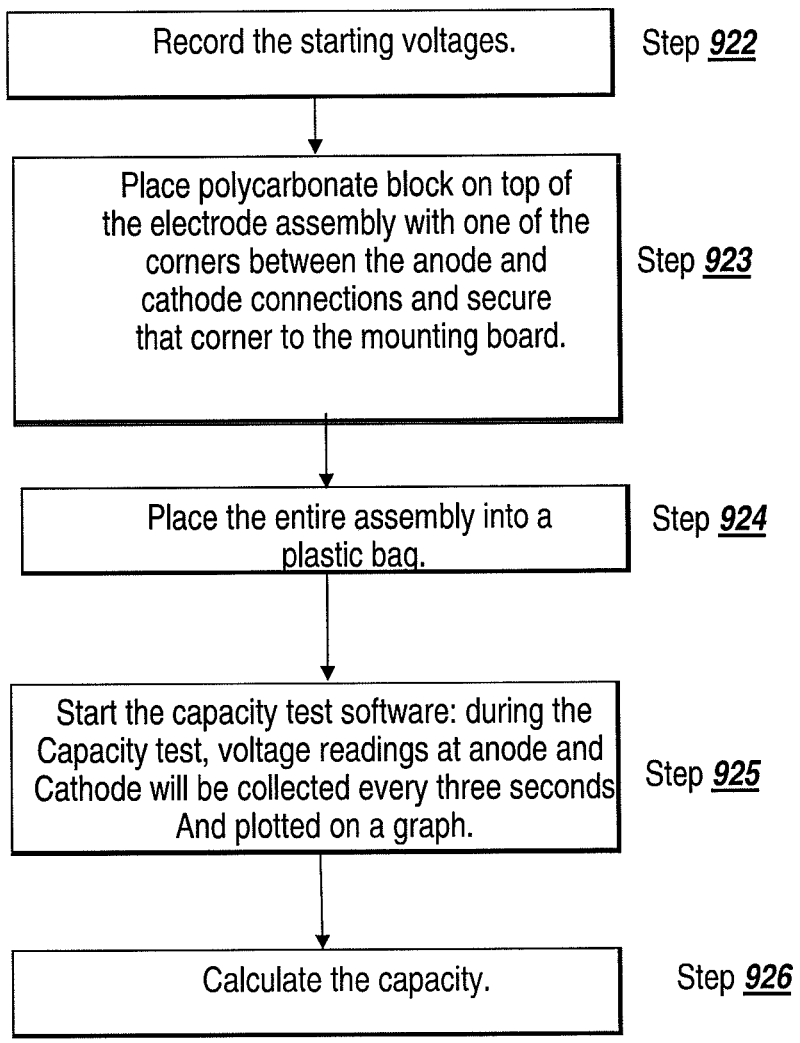

FIG. 13 is a block flow diagram depicting exemplary steps of a method for measuring the capacity. In step 901, a performance evaluation is done on the test assembly by measuring and recording the voltage of the test assembly. For example, test clips are attached to a reference resistor connector and software is provided whereby the voltage across the test assembly is measured and recorded. Continuing with step 901, the voltage is compared to a base or nominal voltage value over specific time intervals. For example, over a time window of 0-12 seconds the nominal voltage is 0.02 v for the anode and −0.02 v for the cathode. A passing measurement for this time interval falls within +/−0.01 v. For the time interval of 15-27 seconds the nominal voltage for the anode is 0.22 v and −0.22 v for the cathode. A passing measurement for this time interval falls within +/−0.02 v. For the time interval of 30-42 seconds the nominal anode voltage is 0.44 v while the nominal cathode voltage is −0.44 v. A passing measurement for this time interval falls within the range of +/−0.02 v. For the time interval of 45-57 seconds, the nominal voltage for anode and cathode are 0.88 v and −0.88 v, respectively. A passing measurement for this time interval falls within +/−0.04 v of those values. For the time interval of 60-72 seconds the nominal anode and cathode voltage are 0.02 v and −0.02 v, respectively. A passing measurement for this time interval falls within +/−0.01 v. In step 902, voltage measurements that fall outside the passing measurements indicate that the test assembly is defective and may be subjected to a retest. Other exemplary embodiments of the drug delivery system 10 contemplate alternative nominal values and passing ranges.

In step 903, a package having both an anode and a cathode is cut such that the anode is separated from the cathode. In step 904, the cathode and the anode are respectively labeled to preserve their identity. In step 905, the anode is placed on a surface, for example, a table. The anode includes an electrode tail and opposing surfaces with one surface having a conductive ink. The anode is placed on the surface such that the conductive ink is facing up and the electrode tail is at the 12 o'clock position. In step 906, with the ink side up, a square printed end of a reference electrode is folded over about ¼ of an inch from the end. In step 907, the reference electrode is placed approximately ¼ of an inch to the side of the labeled anode. The folded end of the reference electrode is projected past the end of the backing in the same direction as the tail of the electrode. In step 908, the reference electrode is secured to a polyester material with a securing mechanism, for example, a piece of tape such that the tape does not contact the electrode ink. In step 909, steps 905 through 908 are repeated for the labeled cathode portion previously separated from the anode.

In step 910, a HPC salt package is opened and the HPC salt pad is used to smear the residue on to the cathode such that substantially all of the surface, preferably 100%, of the cathode electrode circle and the reference electrode are covered. In step 911, using forceps or other type of gripping means, the HPC pad is removed and placed on the cathode. In step 912, the edge of the pad is contacted and rolled onto the cathode, covering the cathode and reference electrode. In step 913, a wet preparation start time is recorded.

In step 914, a polyamine package containing a polyamine pad is opened and using forceps or other type of gripping means. In step 915 the polyamine pad is applied to the HPC pad as described for the HPC pad so that the edges of both the HPC and polyamine pads are aligned. The polyamine residue from the polyamine package is smeared onto the anode covering substantially all the surface of the anode electrode circle. Preferably 100% of the surface is covered. In step 916, the anode is placed on top of the polyamine pad using a rolling method. The conductive ink die is faced down and is in contact with the polyamine pad. The tails of the anode and anode reference electrodes should be offset from the cathode electrode pair by approximately 1 inch.

In step 917, the assembled electrode pair is placed on a mounting board. In step 918, the electrode pair is secured to the mounting board, preferably by tape or other suitable adhesive means. In step 919, the surface of the assembled electrode pair is gently smoothed away to remove any trapped air bubbles. In step 920, the wires from a driver board are attached by clipping a first wire to the anode reference electrode; clipping a second wire to the anode; clipping a third labeled wire to the cathode; and clipping a fourth labeled wire to the cathode reference electrode. In step 921, the voltages for the anode and cathode are verified. For example, valid voltages may fall within the range of −0.9 to −1.2 volts for the anode and 0 to −0.1 volts for the cathode. In step 922, the voltages are recorded. In step 923, a polycarbonate block is placed on top of the electrode assembly with one of the corners between the anode and cathode connections. That corner is secured to the mounting board. In step 924, the entire assembly is then placed into a re-sealable plastic bag. In step 925, the capacity is measured. For example, capacity software is executed for the measurement and recordation of voltage readings at the cathode and anode. In step 926, the capacity of the electrodes is calculated.

In certain other embodiments of the apparatus and the methods of the present invention, the electrotransport current follows a predetermined current-time profile.

In certain other embodiments of the methods disclosed herein, an output voltage applied across the animal body surface is maintained below a maximum value irrespective of changes in a resistance of the animal body surface to avoid burning the animal body surface. In certain other embodiments the methods further comprises the steps of detecting if there is a minimum level of energy in a battery of the device and driving the electrotransport current through the animal body surface only if the battery has the minimum level of energy.

In other embodiments, the method further comprises the steps of shutting down the device upon detecting a potential safety issue and providing an indication that the device has been shut down.

In some embodiments, the indication is the turning off of an LED light in the device. In certain other embodiments the indication is the playing of an audio tone by the device.

Certain other embodiments of the methods disclosed herein further comprises the steps of immediately after turning on the drug delivery device, applying an output voltage across the animal body surface for a predefined time duration without controlling the duty cycle of the PWM power supply.

In other embodiments, the methods comprise controlling the electrotransport current in a predetermined profile, wherein the predetermined profile of the electrotransport current includes a first fixed current value for a first predetermined time duration and a ramp of increasing or decreasing current values for a second predetermined time duration.

In other embodiments, the methods further include controlling the electrotransport current in a predetermined profile, wherein the predetermined profile comprises a first fixed current value for a first predetermined time duration and a second fixed current value for a second predetermined time duration.

Other embodiments of the methods also include controlling the electrotransport current in a predetermined profile, wherein the predetermined profile comprises a ramp over a predetermined time duration beginning at a first current value and ending at a second current value.

In some embodiments of the methods disclosed herein, the first fixed current value is 4 mA and the first predetermined time duration is 1 hour while the second fixed current value is 2 mA and the second predetermined time duration is 3 hours and the predetermined total run-time is 4 hours.

Other embodiments of the methods disclosed herein further comprises detecting if the electrotransport current reaches a minimum level of current within an initial period after switching on the device and switching off the electrotransport current if the electrotransport current does not reach the minimum level of current within the initial period.

In certain other embodiments the method further includes the step of switching on the device one or more times until a battery of the device is depleted.

Other embodiments further comprises the step of controlling the electrotransport current in a predetermined profile, wherein the predetermined profile is selected based on a characteristic of the animal body surface.

In some other embodiments the method further comprises controlling the electrotransport current in a predetermined profile, wherein the predetermined profile is selected based on a characteristic of the therapeutic agent.

In other embodiments of the methods the programming of the controller is changed subsequent to manufacture of the drug delivery device to adapt to a user of the device.

In certain other embodiments the methods further includes the steps of programming the controller to drive the electrotransport current through the animal body surface in a first predetermined profile and changing the programming of the controller to drive the electrotransport current through the animal body surface in a second predetermined profile.

In certain other embodiments of the methods the programming of the controller is changed subsequent to manufacture of the drug delivery device to adapt to a user of the device.

Other embodiments of the methods further comprises the step of adjusting the electrotransport current to account for a change in a resistance of the animal body surface.

In certain other embodiments, the methods further comprises the step of adjusting the electrotransport current to account for a change in a resistance of the animal body surface.

In certain other embodiments, the method further comprises the step of programming the controller to slowly drain the PWM power supply at the end of dosing of the therapeutic agent.

In other embodiments of the invention, a drug delivery device for driving an electrotransport current through an animal body surface is disclosed wherein the device comprising a patch having two electrodes and one or more reservoirs storing a therapeutic agent. The one or more reservoirs is adapted to release the therapeutic agent through the animal body surface when the one or more reservoirs are positioned over the electrodes to form an electrical path for the electrotransport current traveling from one of the electrodes to the other of the electrodes. The device further comprises a controllable power supply for applying an output voltage across the animal body surface and driving the electrotransport current through the animal body surface. The device also comprises a controller programmed to generate one or more interrupts at predetermined intervals, turn off the controllable power supply when the one or more interrupts are generated, drive the electrotransport current through the animal body surface in a predetermined profile, determine a present value of the electrotransport current and a representative value of a target electrotransport current, and control the controllable power supply at least based on the present value and the dynamic value representative of the target electrotransport current.

In certain other embodiments of the device, the controller controls the controllable power supply using a linear regulator. In other embodiments, the patch and the power supply are integrated.

In certain embodiments of the device, the voltage regulator is an inverse single ended primary inductor converter (SEPIC) voltage regulator while in other embodiments the voltage regulator is a standard buck converter voltage regulator. In other embodiments, the voltage regulator is a standard boost converter voltage regulator. In some embodiments, the voltage regulator is a buck-boost converter voltage regulator.

In certain other embodiments, the device further comprises a light-emitting diode (LED) for providing a visual indication to indicate that the device is active.

In other embodiments, the predetermined profile of the electrotransport current comprises a fixed current value for a predetermined time duration. In other embodiments, the predetermined profile of the electrotransport current comprises a first fixed current value for a first predetermined time duration and a ramp of increasing or decreasing current values for a second predetermined time duration.

In other embodiments of the device, the predetermined profile of the electrotransport current comprises a first fixed current value for a first predetermined time duration and a second fixed current value for a second predetermined time duration.

In certain other embodiments of the device, the controller is further programmed to adjust the electrotransport current to account for a change in a resistance of the animal body surface. In certain other embodiments, the controller is further programmed to adjust the output voltage to account for a change in a resistance of the animal body surface.

In certain other embodiments of the device, the potential safety issue is detected during operation of the device if a battery voltage is below a minimum voltage, the minimum voltage being a voltage below which the controller may not function properly.

In other embodiments of the device, the potential safety issue is detected during operation of the device if the electrotransport current is higher than a maximum current for a first predefined time duration.

In some embodiments of the device, the potential safety issue is detected during operation of the device if the electrotransport current is lower than a minimum current for a second predefined time duration while in other embodiments, the potential safety issue is detected during operation of the device if the output voltage is higher than a maximum voltage for a predefined time duration.

One skilled in the art will appreciate further features and advantages of the present invention based on the above-described exemplary embodiments. Accordingly, the present invention is not to be limited by what has been particularly shown and described, except as indicated by the appended claims.

While the methods, systems and apparatuses of the present invention have been particularly shown and described with reference to the exemplary embodiments thereof, those of ordinary skill in the art will understand that various changes may be made in the form and details herein without departing from the spirit and scope of the present invention. Those skilled in the art will recognize, or be able to ascertain using no more than routine experimentation, numerous equivalents to the specific procedures described herein. Such equivalents are considered to be within the scope of the present invention and are covered by the appended claims.

What is claimed is:

1. A drug delivery device for driving an electrotransport current through an animal body surface, the device comprising:
   a patch comprising:
      two electrodes; and
      one or more reservoirs storing a therapeutic agent, the one or more reservoirs releasing the therapeutic agent through the animal body surface when the one or more reservoirs are positioned over the electrodes to form an electrical path for the electrotransport current traveling from one of the electrodes to the other of the electrodes;
   a controllable power supply for:
      applying an output voltage across the animal body surface; and
      driving the electrotransport current through the animal body surface; and
   a controller programmed to:
      determine a present value of the electrotransport current;
      determine a dynamic value representative of a target electrotransport current, the dynamic value determined based on the target electrotransport current, a resistance value of a sense resistor used to detect the electrotransport current flowing between the electrodes, a value of a bandgap voltage associated with the controller, and a fixed voltage value; and
      control the controllable power supply at least based on the present value of the electrotransport current and the dynamic value representative of the target electrotransport current.

2. The device of claim 1, wherein the controller controls the controllable power supply using a linear regulator.

3. The device of claim 2, wherein the controller is further programmed to:

shut down the device upon detecting a potential safety issue; and provide an indication that the device has been shut down.

4. The device of claim 1, wherein the controller controls the controllable power supply using a switching regulator.

5. The device of claim 4, wherein the switching regulator performs pulse width modulation (PWM) and the controllable power supply is a PWM power supply.

6. The device of claim 5, wherein the controller is programmed to:
control a duty cycle of the PWM power supply at least based on the present value of the electrotransport current and the dynamic value representative of the target electrotransport current.

7. The device of claim 5, wherein the controller is further programmed to:
determine the present value of the electrotransport current and the dynamic value representative of the target electrotransport current at predetermined intervals using a timer.

8. The device of claim 5, wherein the controller is further programmed to:
determine a present value of the output voltage;
determine a dynamic value representative of a target output voltage;
perform a first comparison between the present value of the output voltage and the dynamic value representative of the target output voltage;
perform a second comparison between the present value of the electrotransport current and the dynamic value representative of the target electrotransport current; and
control a duty cycle of the PWM power supply based on the first comparison or the second comparison.

9. The device of claim 8, wherein control of the duty cycle of the PWM power supply further comprises:
determining that the present value of the output voltage is greater than the dynamic value representative of the target output voltage based on the first comparison; and
reducing the duty cycle of the PWM power supply by one step without performing an electrotransport current correction.

10. The device of claim 8, wherein control of the duty cycle of the PWM power supply further comprises:
determining that the present value of the output voltage is less than or equal to the dynamic value representative of the target output voltage based on the first comparison; and
performing an electrotransport current correction based on the second comparison.

11. The device of claim 10, wherein performing the electrotransport current correction comprises:
determining that the present value of the electrotransport current is greater than the dynamic value representative of the target electrotransport current based on the second comparison; and
reducing the duty cycle of the PWM power supply by one step.

12. The device of claim 10, wherein performing the electrotransport current correction comprises:
determining that the present value of the electrotransport current is equal to the dynamic value representative of the target electrotransport current based on the second comparison; and
maintaining the duty cycle of the PWM power supply at its present step.

13. The device of claim 10, wherein performing the electrotransport current correction comprises:
determining that the present value of the electrotransport current is less than the dynamic value representative of the target electrotransport current based on the second comparison; and
increasing the duty cycle of the PWM power supply by one step.

14. The device of claim 1, wherein the patch and a power supply are separable.

15. The device of claim 1, wherein the controller is further programmed to:
detect if there is a minimum level of energy in a power supply of the device; and
drive the electrotransport current through the animal body surface only if the power supply has the minimum level of energy.

16. The device of claim 1, wherein the controller is re-programmable to drive the electrotransport current through the animal body surface in a second predetermined profile.

17. The device of claim 1, wherein the controller is further programmed to:
maintain the output voltage below a maximum level irrespective of changes in the resistance of the animal body surface.

18. The device of claim 1, wherein the device is configured for a single use, and wherein the controller is programmed to slowly drain a power supply at the end of dosing of the therapeutic agent.

19. The device of claim 1, wherein the dynamic value representative of the target electrotransport current is determined based at least on the target electrotransport current and an operational characteristic of a power supply that varies during operation of the power supply.

20. The device of claim 19, wherein the operational characteristic of the power supply is a variable output voltage of the power supply.

21. The device of claim 19, wherein the dynamic value representative of the target electrotransport current is determined based at least on the target electrotransport current and a reference voltage at an analog-to-digital converter that varies during operation of the power supply.

22. A method of delivering a drug to a user, the method comprising administering the drug using the device of claim 1.

23. A method of treating a user, the method comprising transdermally administering to the user an effective amount of a drug, wherein the drug is administered using the device of claim 1.

24. The method according to any of claims 22-23, wherein the drug is a triptan compound.

25. A method of treating a triptan compound responsive state in a user, the method comprising transdermally administering to the user an effective amount of a triptan compound, wherein the triptan compound is administered using the device of claim 1.

26. The method according to claim 25, wherein the triptan compound responsive state is at least one state selected from the group consisting of migraines, familiar hemiplegic migraines (with and without aura), chronic paroxysmal headaches, cluster headaches, migraine headaches, basilar migraines, and atypical headaches accompanied by autonomic symptoms.

27. The method according to claim 26, wherein the triptan compound is sumatriptan succinate.

* * * * *